United States Patent [19]

Levy

[11] Patent Number: 4,983,390
[45] Date of Patent: Jan. 8, 1991

[54] TERRESTRAIL DELIVERY COMPOSITIONS AND METHODS FOR CONTROLLING INSECT AND HABITAT-ASSOCIATED PEST POPULATIONS IN TERRESTRIAL ENVIRONMENTS

[75] Inventor: Richard Levy, Fort Myers, Fla.

[73] Assignee: Lee County Mosquito Control District, Fort Myers, Fla.

[21] Appl. No.: 210,792

[22] Filed: Jun. 24, 1988

Related U.S. Application Data

[63] Continuation-in-part of Ser. No. 32,532, Apr. 1, 1987, Pat. No. 4,818,534.

[51] Int. Cl.⁵ .................... A01N 25/34; A61K 9/14
[52] U.S. Cl. ................... 424/404; 424/405; 424/408; 424/409; 424/78; 424/84; 424/410
[58] Field of Search ............. 424/405, 408, 410, 409, 424/78, 84; 71/3

[56] References Cited

U.S. PATENT DOCUMENTS

| | | | |
|---|---|---|---|
| 3,085,850 | 4/1963 | Egan et al. | 21/60.5 |
| 3,231,443 | 1/1966 | McNulty | 156/187 |
| 3,415,614 | 10/1968 | Egan et al. | 21/60.5 |
| 3,535,423 | 10/1970 | Ordas | 424/176 |
| 3,576,760 | 4/1971 | Gould et al. | 424/487 X |
| 3,823,045 | 7/1974 | Hielema | 156/188 |
| 3,957,480 | 5/1976 | Kornis | 424/405 X |
| 4,053,627 | 10/1977 | Scher | 424/278 |
| 4,058,124 | 11/1977 | Yen et al. | 424/79 |
| 4,062,855 | 12/1977 | Allan et al. | 424/78 |
| 4,070,348 | 1/1978 | Kraemer et al. | 424/484 X |
| 4,094,715 | 6/1978 | Henderson et al. | 156/195 X |
| 4,110,431 | 8/1978 | Oita | 424/78 |
| 4,134,863 | 1/1979 | Fanta et al. | 128/285 |
| 4,154,818 | 5/1979 | Kanada et al. | 424/81 |
| 4,160,033 | 7/1979 | Garrett et al. | 424/285 |
| 4,182,620 | 1/1980 | Denninger et al. | 71/65 |
| 4,192,697 | 3/1980 | Parker et al. | 156/188 |
| 4,211,595 | 7/1980 | Samour | 156/187 |
| 4,244,728 | 1/1981 | DelliColli et al. | 424/405 X |
| 4,267,280 | 5/1981 | McCormick | 525/56 |
| 4,304,591 | 12/1981 | Mueller et al. | 424/484 X |
| 4,344,857 | 8/1982 | Shasha et al. | 252/316 |
| 4,349,553 | 9/1982 | Brown | 424/484 X |
| 4,375,535 | 3/1983 | Kightlinger et al. | 424/285 X |
| 4,400,391 | 8/1983 | Connick, Jr. | 71/88 |
| 4,401,456 | 8/1983 | Connick, Jr. | 424/488 X |
| 4,421,759 | 12/1983 | Boisvenue | 424/405 X |
| 4,427,725 | 1/1984 | Crofts | 428/36 |
| 4,436,719 | 3/1984 | Lindaberry | 424/407 |
| 4,497,930 | 2/1985 | Yamasaki et al. | 524/556 |
| 4,500,338 | 2/1985 | Young et al. | 424/484 X |
| 4,510,007 | 4/1985 | Stucke | 156/244.12 |
| 4,510,181 | 4/1985 | Okuno et al. | 427/388.2 X |
| 4,521,470 | 6/1985 | Overbergh et al. | 156/86 X |
| 4,525,414 | 6/1985 | Ohya et al. | 428/913 X |
| 4,568,400 | 2/1986 | Patterson, Jr. et al. | 427/120 |
| 4,574,023 | 3/1986 | Edwards et al. | 156/187 |
| 4,634,615 | 1/1987 | Versteegh et al. | 156/86 X |
| 4,639,366 | 1/1987 | Heller | 424/484 |
| 4,640,044 | 2/1987 | Varnon | 424/405 X |
| 4,663,341 | 5/1987 | Jacobson | 514/256 X |
| 4,663,346 | 5/1987 | Coulston et al. | 514/456 |
| 4,667,436 | 5/1987 | Benson | 424/405 X |
| 4,677,003 | 6/1987 | Redlich et al. | 71/3 X |
| 4,681,806 | 7/1987 | Matkan et al. | 71/3 X |
| 4,707,359 | 11/1987 | McMullen | 71/3 X |
| 4,707,388 | 11/1987 | Park et al. | 427/385.5 X |
| 4,722,838 | 2/1988 | Tocker | 424/405 X |
| 4,729,920 | 3/1988 | McLoughlin et al. | 156/86 X |
| 4,743,448 | 5/1988 | Bahadir et al. | 424/405 |
| 4,818,534 | 4/1989 | Levy | 424/405 X |
| 4,818,536 | 4/1989 | Meyers et al. | 424/409 |

FOREIGN PATENT DOCUMENTS 2108517 5/1983 United Kingdom .
2141023 12/1984 United Kingdom .

OTHER PUBLICATIONS

*The Insecticide, Herbicide, Fungicide Quick Guide*, B. G. Page et al., Thomson Publications, 1987.
*Insect Control Guide*, Florida Agricultural Extension Service, Institute of Food and Agricultural Sciences University of Florida, Gainsville.
*Agricultural Chemicals* Book I, "Insecticides, Acaricides and Ovicides", W. T. Thomas, 1985–1986 Revision, Thomson Publications.
*Agricultural Chemicals* Book II, "Herbicides", W. T. Thomson, 1986–1987 Revision, Thomson Publications.
*Agricultural Chemicals* Book III, "Fumigants, Growth Regulators, Repellents, and Rodenticides", W. T. Thomson, 1986 Revision, Thomson Publications.
*CRC Handbook of Natural Pesticides*, vol. III, "Insect Growth Regulators", Parts A and B, E. David Morgan et al., CRC Press, including an Introduction and Index Portion.
*Freshwater Vegetation Management*, Edward O. Gangstad, Thomson Publications, 1986.
*Flies of Public Health Importance*, CDC Training Guide, Insect Control Series, U.S. Department of Health, Education and Welfare, H. G. Scott et al., Apr. 1958.

(List continued on next page.)

Primary Examiner—Thurman K. Page
Attorney, Agent, or Firm—Finnegan, Henderson, Farabow, Garrett & Dunner

[57] ABSTRACT

Superabsorbent solid organic polymers (such as acrylamide and acrylate polymers, co-polymers and terpolymers, optionally grafted) which absorb over 100 times their weight in water are used in natural or artificial, terrestrial environment insect (such as fire ants) or pest population control compositions. Methods for using the solid or flowable superabsorbent polymer insecticidal/pesticidal delivery agents for the control of terrestrial insect or pest populations or for the simultaneous or concurrent control of both terrestrial insect and habitat-associated/related pest populations, in an area needing terrestrial environment insect and/or pest control treatment are described.

27 Claims, No Drawings

OTHER PUBLICATIONS

*Guidelines for the Control of Insect and Mite Pests of Foods, Fibers, Feeds, Ornamentals, Livestock, and Households,* U.S. Department of Agriculture, Agricultural Research Service, Agriculture Handbook, No. 584, Jan. 1982.
Scientific Guide to Pest Control Operations, Second Edition (Revised), L. C. Truman et al., Purdue University, 1967.
*Aquatic and Wetland Plants of Florida,* D. P. Tarver et al., Bureaue of Aquatic Plant Research and Control, Florida Department of Natural Resources, 1978.
*Complete Guide to Pest Control—With and Without Chemicals,* G. W. Ware, Thomas Publications, 1980.
*Herbicide Handbook* of the Weed Science Society of America, Fifth Edition, 1983.
*Technical Bulletin* relating to "Sonar®", Herbicide, Elan Co Products Company.
*Technical Bulletin* relating to "Scout TM", Herbicide for Broad Spectrum Aquatic Weed Control, Monsanto Company.
*Technical Bulletin* relating to "System L", and 'System E', Aquatic Herbicides, 4-D Products, Inc.
*Technical Bulletin* relating to "Agricultural Intermediates", Emulsifier, Spray Adjuvants, Surfactants, Dispersants, Polymers of Agricultural Applications, Rohm Haas Company.
*Technical Bulletin,* relating to "Terra-Sorb", including MSDS on Terra-Sorb, Terra-Sorb AG, GB, HB and 200G.
*Product Bulletin,* relating to "SANWET®", including MSDS on SANWET IM-1500, 1500P, 1500F and 1000.
CULIGEL TM SP Superabsorbent Polymer Label and Research and Development Update: CULIGEL TM SP Superabsorbent Polymer.
*Technical Bulletin* relating to "Hydrothol® 191," Granular Aquatic Algaecide and Herbicide, Pennwalt.
*Technical Bulletin* relating to "Komeen®", Aquatic Herbicide, Sandoz, Inc.
*Techical Bulletin* relating to "K-Tea" Algaecide, Cocide Chemical Corporation.
*Technical Bulletin* relating to "Morwet® EFW Powder", Surfactant, DeSoto, Inc.
*Technical Bulletin* relating to "Poly Control 2", Sticker and Drift Control Agent for Pesticides, JLB International, Inc.
*Technical Bulletin* relating to "Rhodia 2,4-D Gran 20", Herbicide, Rhone-Poulenc Chemical Company.
*Technical Bulletin* relating to "Revenge#," Systemic Herbicide, Hopkins Agricultural Company.
*Technical Bulletin* relating to "Banvel® 720", Herbicide, Velsicol Chemical Corp.
*Technical Bulletin,* "Chem-trol TM," Spray Additive Deposition and Drift Retardant, Loveland Industries, Inc.
*Product Bulletin* relating to "Ortho Diquat Herbicide—H/A", Chevron Chemical Company.
*Technical Bulletin* relating to "Dissolvo TM -45", a Water Soluble, Heat Sealable, Stable Pounching Material, Gilbreth International Corp.
*Technical Bulletin* relating to "Fenoxycarb", Insect Growth Regulator, Maag.
*Technical Bulletin* relating to "Ferro-Tech", Agglomeration Equipment, Ferro-Tech.
*Technical Bulletin* relating to "Hydout TM", Aquatic Weed Killer, Pennwalt Corp.
*Technical Bulletin,* relating to "Cytrol® Amitrole-T," Liquid Weed Killer.
*Technical Bulletin* relating to "Aquathol®K", Aquatic Herbicide.
*Technical Bulletin* relating to "Casoron®, G-10", Herbicide, Aquatic Weed Control.
*Technical Bulletin* relating to "Cutrine®-plus.", Algaecide/Herbicide.
*Technical Bulletin* relating to "A and V—70 Granular", Granulated Algaecide.
*Technical Bulletin* relating to "Aquazine®", Algaecide, for Control of Algae and Certain Pond Weeds, Ciba-Geigy.
*Technical Bulletin* relating to "Aquastore®", Soil Additive, Cyanamid. Including MSDS on Aquastore® 1, 2, 3 Soil Water Retention Aid and Aquastore Absorbent Polymer.
*Material Safety Data Sheet,* "Super Sorb", Super Absorbent Company, Inc.
*Technical Data* relating to "Super Slurper" from U.S. Department of Agriculture.
*Technical Data* relating to "Water Lock®," including A-100 Series, G-100 Series, L-Series, B-200 Series, and J-500 Series.
*Technical Data,* relating to "Aridall" including 1080, 1078, 1091, 1092, and 1098.
*Technical Bulletin,* relating to "Adjuvant List", State of Florida, Department of Natural Resources.
*Report* relating to "Agrigel", Hazelton Raltech, Inc.
*Technical Bulletin,* relating to "Aquashade", Aquatic Plant Growth Control.
*Techical Bulletin,* relating to "Amine 6D" Herbicide, Asgrow Florida Company.
Levy et al., "Effect of Water Quality on the Efficacy of Water-Base Suspensions of Arosurf® MSF Against Larvae of *Aedes taeiorhynchus:* Bioassay Evaluations", *Journal of the American Mosquito Control Association,* vol. 3, No. 6, pp. 631-641, Dec. 1987.
Klier et al., "Solute and Penetrant Diffusion in Swellable Polymers. VIII. Influence of the Swelling Interface Number on Solute Concentration Profiles and Release", *Journal of Controlled Release,* 7, (1988), 61-68.
Roorda et al., "Zero-Order Release of Oxprenolol-HCl, A New Approach", *Journal of Controlled Release,* 7, (1988), 45-52.
Kamal et al., "UPTAKE of $^{14}$C-Simetryn by Duckweed (lemna minor) during Release from a Polymer Matrix and the Consequent Herbicidal Effects", *Journal of Controlled Release,* 7, (1988), 39-44.
Wing et al., "Amylose Content of Starch Controls the Release of Encapsulated Bioactive Agents", *Journal of Controlled Release,* 7, (1988), 33-37.
Trimnell et al., "Autoencapsulation: A New Method for Entrapping Pesticides Within Starch", *Journal of Controlled Release,* 7, (1988), 25-31.

(List continued on next page.)

OTHER PUBLICATIONS

*Modern Mosquito Control*, 5th Addition, Cyanamid.

Proceedings of the 14th International Symposium on Controlled Release of Bioactive Materials, (1987), Controlled Release Society, Inc., selected proceedings including pp. 158–167, 202–210, 244–252, 284–292 and 310, including a copy of the Table of Contents.

Program and Abstracts of 15th International Symposium on Controlled Release of Bioactive Materials, held in Basel, Switzerland, Aug. 15–19, 1988, including paper Nos. 15, 17, 19, 20, 23, 27, 30, 31, 55, 110, 130, 135, 139, 152, 170, 171, 173, 175, 190, 191, 195, 201, 204 and 262.

Levy et al., "Control of Immature Mosquitoes with a Single-, Joint-, or Multi-Action Polymer–Base Insecticide Delivery System," presented at the 15th International Symposium on Controlled Release of Bioactive Materials held in Basel, Switzerland, Aug. 15–19, 1988.

Levy et al., "Control of Immature Mosquitoes with a Single-, Joint-, or Multi-Action Polymer–Base Insecticide Delivery System," presented at the 18th International Congress of Entomology, University of British Columbia, Vancouver, BC, Canada, Jul. 3–9, 1988.

"Super Slurper", Mar. 1988, *Popular Science*, p. 9, article discloses the Use of Nematodes in Combination with Super Slurper for Use on Citrus Roots before Planting to Control Weevils.

Hester, "Field Phytotoxicity Studies with Arosurf® MSF", Department of Health and Rehabilitative Services, West Florida Arthropod Research Laboratory.

Axtell et al., "Encapsulation of the Mosquito Fungal Pathogen *Lagenidium giganteum* (OOMYCETES:-LAGENIDIALES) in Calcium Alginate," *Journal of the American Mosquito Control Association*, vol. 3, No. 3, pp. 450–459, Sep. 1987.

O'Neill, "Membrane Systems", *Controlled Release Technologies*, Chapter 4, pp. 129–182.

Kydonieus, "Other Controlled Release Technologies and Application", *Controlled Release Technologies*, Chapter 13, pp. 235–257.

Thomson, "A Guide to Agricultural Spray Adjuvants Used in the United States", 1986 edition, including a copy of Table of Contents and selected pp. 50, 105, 107, 109, 111, 112, 154 and 155.

Levy et al., "Experimental Joint Action Formulations of Arosurf® MSF and *Bacillus thuringiensis* Var. Israelensis or *Bacillus sphaericus*", presented at *1987 AMCA meeting Seattle, Wash., Mar. 29–Apr. 2.*

Levy et al., "Laboratory Evaluations of Experimental Formulations of Arosurf® MSF and *Bacillus thuringiensis* Var. Israelensis, *Bacillus sphaericus* or Abate® 4-E," presented at 1987 FAMA meeting Palm Beach, Fla., May 31–Jun. 3.

Morrill, *Journal of the American Mosquito Control Association*, News and Notes, pp. 565–566, vol. 2, No. 4, Dec. 1986, cites a Newsweek article giving a Brief Mention to the Possibility of "Microsponges" for the Release of Insect Repellents, including copy of Table of Contents.

Miller, "Dimensionally Stable Soluble Pouches for Safety", Pesticide Formulations and Application System, vol. 8, American Society for Testing and Materials, 1988.

*FRASS Newsletter*, vol. 8, No. 1, 1985, discloses a Starch Graft Polymer (SGP) called "Super Slurper" for Use in Coating Seeds, Preventing Soil Erosion, Fighting Fires, and Absorbing Chemical Spills.

"AROSURF® MSF," Mosquito Larvicide and Pupicide, Technical Bulletin on this Product as Mosquito Control Treatment.

Technical Bulletin, "TEKNAR®," Larvicide for Mosquito and Blackfly Control prepared from *Bacillus thuringiensis* berliner, var. israelensis.

Technical Bulletin, "VECTOBAC-G®," Granular Formulation of *Bacillus thuringiensis* formulated as Granules with a Carrier of Corn Cob Particles.

"PYRENONE®, TOSSITS®," encapsulated Larvicide.

"Bactimos Briquet," a Sustained Release Mosquito Control Product.

Baines, "Biodegradation of Polyvinyl Alcohol" and Bryan et al., Biodegradation of Synthetic Warp Sizes.

Technical Bulletin, Water Soluble Films, including "Quik Sol A and P, Edisol-m, EM-1100, QSA 2000 and Mono-Sol".

Leppla, "Gelling Agents for Insect Diet: From Mush to Medium", Discussion of Natural Thickeners and their Chemical Structures.

"Altosid® Briquet, Product Application Bulletin", Technical Bulletin, No. 1115-81-2, Zoecon Corporation, Formulation Designed to Time Release Insect Growth Regulator.

*Material Safety Data Sheet*, Grain Processing Corporation, Water Lock® Superabsorbent Polymer "G" Series.

*Data Sheet*, Super Absorbent Company, Super Sorb.

*Material Safety Data Sheet*, "Terra-Sorb".

*Material Safety Data Sheet*, "Terra-Sorb GB".

*Product Data Sheet*, "Water Lock G-100 Superabsorbent Polymer", Grain Processing Corporation.

SGP®, "Safety of SGP® 502S Absorbent Polymer", Material Published from General Mills Chemical Inc.

Prichard et al., "Super Soil Moisturizer Challenges Others in Growing Industry", *Ornamentals South*, edited from a speech to the American Institute of Landscape Architects, Las Vegas, Nev., Aug. 22, 1981.

Del Deterling, "Super Slurper Gets Your Crop Moving Earlier", *Progressive Farmer*, Feb., 1981.

Weaver et al., "A Practical Process for the Preparation of Super Slurper, a Starch Based Polymer with a Large Capacity to Absorb Water", *Die Starke 29.Jahrg.1977/Nr. 12,S.413–422.*

"Super Slurper: Compound with a Super Thirst", Reprinted from *Agricultural Research*, Jun. 1975, Published by the U.S. Department of Agriculture.

Whitemore, "Transplant Survival Improved", *Christmas Trees*, vol. 10, No. 1, Jan. 1982.

Burgess et al., "A New Method for Applying Arosurf® MSF (Monomolecular Surface Film Formulations)", *Journal of American Mosquito Control Association*, vol. 1, No. 2, pp. 245–247, Jun. 1985.

Levy et al., "Effect of Low Temperature on the Mosquito Larvicide and Pupicide Arosurf® MSF (Monomolecular Surface Film) and Adol® 85, (Indicator (List continued on next page.)

OTHER PUBLICATIONS

Oil): Physical Evaluations", *Mosquito News*, vol. 44, No. 3, pp. 419–422, Sep. 1984.
Levy et al., "Florida Mosquito Control Districts Use Arosurf® 66-E2", *Pest Control*, Field Guide, Apr., 1983.
Levy et al., "Comparative Efficacy of Technology and Water-Base Formulation of Arosurf® MSF Against *Aedes taeniarhynchus*", *Journal of American Mosquito Control Association*, vol. 2, No. 4, pp. 560–562, Dec. 1986.
Levy et al., "Laboratory Evaluations of Formulations of Arosurf® MSF and *Bacillus sphaericus* Against Larvae and Pupae of *Culex quinquefasciatus*", *Journal of American Mosquito Control Association*, vol. 2, No. 2, pp. 233–236, Jun. 1986.
Levy et al., "Control of Immature Mosquitoes Through Applied Surface Chemistry", *Proceedings of the Florida Anti-Mosquito Association*, vol. 51, No. 2, pp. 68–71.
Levy et al., "Investigations on the Mosquito Control Potential of Formulations of Arosurf® MSF and Conventional Larvicides", *Mosquito News*, vol. 44, No. 4, pp. 592–595, Dec. 1984.
Levy et al., "Efficacy of Arosurf® MSF (Monomolecular Surface Film) Base Formulations of *Bacillus thuringiensis* Var. Israelensis against the Mixed Populations of Mosquito Larvae and Pupae: Bioassay and Preliminary Field Evaluations", *Mosquito News*, vol. 44, No. 4, pp. 537–543, Dec. 1984.
Levy et al., "Additional Studies on the Use of the Monomolecular Surface Film Arosurf® 66-E2 for Operational Control of Mosquito Larvae and Pupae", *Journal of Florida Anti-Mosquito Association*, vol. 53, No. 2, pp. 100–106, 1982.
Hertlein et al., "An Injection Method for Spraying Biological Control Agents and a Monomolecular Surface Film for Control of Immature Mosquitoes", *Journal of American Mosquito Control Association*, vol. 1, No. 2, pp. 255–257, Jun. 1985.
Levy et al., "Efficacy of the Organic Surface Film Isostearyl Alcohol Containing Two Oxyethylene Groups for Control of Culex and Psorophora Mosquitoes: Laboratory and Field Studies", *Mosquito News*, vol. 42, No. 1, pp. 1–11, Mar. 1982.
Levy et al., "Control of Larvae and Pupae of *Anpoheles quadrimaculatus* and *Anopheles crucians* in Natural Paludal Ponds with the Monomolecular Surface Film Isostearyl Alcohol Containing Two Oxyethylene Groups", *Mosquito News*, vol. 42, No. 2, pp. 172–178, Jun. 1982.
Levy et al., "Ground and Aerial Application of a Monomolecular Organic Surface Film to Control Salt-Marsh Mosquitoes in Natural Habitats of Southwestern Florida", *Mosquito News*, vol. 41, No. 2, pp. 291–301, Jun. 1981.
Levy et al., "Persistence of the Mosquito Larvicide and Pupicide Arosurf® MSF in Permanent and Semi-Permanent Habitats", *Journal of Florida Anti-Mosquito Association*, vol. 56, No. 1, pp. 32–36, 1985.
Levy et al., "Formulations for Enhancing the Mosquito Larvicidal Action and Persistence of the Monomolecular Surface Film Isostearyl Alcohol Containing Two Oxyethylene Groups (Aro-surf® MSF", *Journal of Florida Anti-Mosquito Association*, vol. 55, No. 1, pp. 31–34, 1984.
Harwood et al., Entomology in Human and Animal Health, Seventh Edition, 1979, Macmillan Publishing Co., Inc., New York, N.Y., title page and table of contents.
Agis F. Kydonieus, *Controlled Release Technologies: Methods, Theory, and Applications*, vols. I and II, 1980, CRC Press, Inc., Boco Raton, Fla., and specifically pp. 1 through 19 and 116 through 127 of vol. I, which relate to information on controlled release in general and specifically to Herbicides; pp. 240 through 246 of vol. I, which relate to controlled Release from Ultramicroporous Triacetate; vol. II, pp. 241 through 257, which relate to controlled release from Gels including a list of cited patent literature; and pp. 8 through 62 of vol. II, which relate to the biodegradative controlled release of Pesticides from Polymeric Substrates, as well as a copy of the detailed Table of Contents.
Richard Baker, *Controlled Release Technologies of Biologically Active Agents*, 1987, John Wiley & Sons, New York, N.Y., pp. 177–191, as well as the detailed Table of Contents.
Levy et al., "Control of Immature Mosquitoes with Liquid and Solid Formulations of a Monomolecular Organic Surface Film", presented at the Joint Meeting of the American Mosquito Control Association and California Mosquito and Vector Control Association, Apr. 18–22, 1982, Sacramento, Calif., pp. 106–108.

TERRESTRAIL DELIVERY COMPOSITIONS AND METHODS FOR CONTROLLING INSECT AND HABITAT-ASSOCIATED PEST POPULATIONS IN TERRESTRIAL ENVIRONMENTS

CROSS-REFERENCE TO RELATED APPLICATION

This is a continuation-in-part of my application entitled "Improved Insecticidal Delivery Compositions and Methods for Controlling a Population of Insects in an Aquatic Environment," Ser. No. 032,532 filed Apr. 1, 1987, now U.S. Pat. No. 4,818,534.

BACKGROUND AND SUMMARY OF THE INVENTION

1. Field of the Invention

The present invention relates to a facile method of applying a solid or flowable (aqueous or oil base) terrestrial delivery composition with one or more active insecticidal ingredients, with or without additional nontoxic ingredients, to control a variety of terrestrial (i.e., non-aquatic) insects or pests ((mainly insects and their close relatives (Arthropoda) as well as rodents (Muridae), nematodes, fungi, and weeds)) that are pests of ornamentals and turf, livestock, forest and shade trees, field crops and pastures, fruits and nuts, households, poultry, stored products, and vegetables with conventional ground or aerial techniques.

This invention further relates to a facile method of combining, mixing, encapsulating, agglomerating, or formulating one or more superabsorbent polymers with two or more active insecticidal or pesticidal ingredients, optionally with water, with or without various nontoxic adjuvants, diluents or carriers, etc., into solid powders, dusts, granules, pellets, extrusions or briquets, and/or into aqueous (or oil base) flowable, variable-viscosity sols or semi-gels. The use of superabsorbent polymers in this manner makes possible the mixing or application of insecticidal ingredients or pesticidal ingredients, with or without other additives, that would otherwise be difficult or substantially impossible to combine as joint- or multiple-action solid or flowable formulations.

The present invention also relates to a solid (i.e., powdered, extruded, flaked, granular, pelleted, briquetted) or variable-viscosity, flowable (i.e., sprayable, pumpable, injectable) terrestrial pest control delivery composition made from one or more solid superabsorbent polymers with or without water, and with one or more insecticidial agents, such as insecticides, ovicides, larvicides, pupicides, biological control agents, pathogens, parasites, microbial control agents, insect growth regulators, conventional toxicants, fumigants, systemics, chemosterilants, pheromones, attractants, repellents, or with one or more solid or liquid pesticidal agents such as acaricides, miticides, pesticides, herbicides, hormones, sterilants, bactericides, fungicides, nematicides, avicides, rodenticides, molluscicides, or predicides, or mixtures thereof, with or without one or more nontoxic adjuvants, diluents, or enhancers, such as carriers, baits, binders, deflocculating agents, fertilizers, penetrants, preservatives, spreading agents, surface-active agents, surfactants, suspending agents, wetting agents, stabilizing agents, compatability agents, sticking agents, waxes, oils, inverting oils, co-solvents, coupling agents, foams, antifoaming agents, synthetic plastics, elastomers, synergists, natural or synthetic polymers; and other additives and mixtures thereof.

In particular, the present invention is directed toward a method of formulating and applying one or more superabsorbent polymers with one or more insecticidal agent(s), and one or more pesticidal agent(s), with or without water or other additives, into solid powders, dusts, granules, pellets, extrusions, or briquets, or into flowable, variable-viscosity compositions such as sols or semigel-like formulations that can produce quick, slow, controlled, prolonged, or extended release of the active ingredients to simultaneously or concurrently control a variety of mature or immature terrestrial insects, and other non-insect pests in a variety of terrestrial habitats with a single application of a solid or flowable multi-product formulation.

Mode of action (e.g., fumigant, contact, slow-release, stomach poison, systemic, bait, etc.) will be dependent on the type(s) of insecticide(s), pesticide(s) and polymer(s) used in the solid or flowable compositions, the type of terrestrial habitat, and the species of insect(s) or pest(s) to be controlled. Release of the active agent(s) is via a polymer matrix water activation/swelling/diffusion mechanism and by environmental degradation of the polymer encapsulation matrix.

2. Discussion of the Prior Art

U.S. Pat. Nos. 4,400,391 and 4,401,456 disclose the use of alginate gel beads to encapsulate bioactive materials to provide for their controlled release. The patents describe beads being made to either float or sink (if used in an aqueous environment) and they may contain herbicides. These beads are also described as acting as carriers to place the bioactive material near the target species, for example, a floating bead containing a herbicide releasing the herbicide, in close proximity to floating aquatic weeds, or the beads falling through foliage to release herbicide into the soil.

U.S. Pat. No. 4,344,857 involves encapsulation by xanthate derivatives. The encapsulation techniques are complicated, costly and quality sensitive.

Gould et al U.S. Pat. No. 3,576,760, describes a method for entrapping fragrances, detergents, enzymes, food flavors and pesticides in a water soluble polymer. The entrapment is described as accomplished by mutually dissolving the water soluble polymer and the entrapped additive, which are then dried (e.g., spray dried). The primary purpose of this technique is to protect the entrapped species prior to target delivery. The polymers instantly dissolve in water and as such are unsuitable for controlled release. The technique is further limited in the types and quantities of entrapable compounds.

Mueller et al., U.S. Pat. No. 4,304,591, employs an allegedly novel free radical polymerized hydrogel. The ingredients are incorporated into the hydrogel primarily by presence in the polymerization solution, however some medicants are stated as suitably diffused into the matrix via a solvent medium thereafter. This method is limited in both the capacity of the hydrogel matrix and its ability to incorporate diverse, and potentially incompatible agents. The major effective use contemplated for this matrix is the delivery of medicants.

A U.K. Patent No. 2,108,517, discloses a hydrogel having at least one polymerizable cyclic (thio)ether and at least one hydrophilic homo-or co-polymer. This composition like Mueller et al. is stated as being particularly suited to slow release of medicants, particularly for treatment of tropical diseases.

A relatively new approach to insecticidal and pesticidal delivery has been by application of controlled-release formulations, to varying degrees of success, such as described by Richard W. Baker in *Controlled Release of Biologically Active Agents*, 1987, Wiley-Interscience Publishing, 279, pp. This text generally describes the use of various controlled release technologies including simple diffusion from monolithic devices such as hydrogels. However, this method is normally limited by hydrogel capacity and difficulties with incorporation of the desired agent, particularly hydrophilic substances. The capacity and incorporation problems with monolithic devices are often addressed by reservoir devices. More complex release mechanism include the use of biodegradable matrix carriers, namely, bonding of active ingredients in heterogeneously or homogeneously degradable polymers, called polyagents. Polyagents may actually be polymers formed of monomers of the active agent. The release mechanics of these controlled release mechanisms are complex, depending on the presence (and strength) or absence of degradable ligand bonds and their location (e.g., as active agent bonds to the polymer), concentration of the active agent and/or dispersant or solvent in the carrier, the relative hydrophobicity or hydrophilicity of the polymer, whether or not the polymer degrades homogeneously or heterogeneously, whether the active agent is in the solid form or liquid form in the polymer, etc. Further formation of such polyagents is complicated and often reagent specific.

SPECIFIC OBJECTS

It is an object of the present invention to provide insecticidal, pesticidal, or insecticidal/pesticidal compositions, and a method of application, that are solid or flowable, and methods for the ground or aerial treatment of a variety of terrestrial habitats which overcome the problems and deficiencies of the prior art.

It is also an object of the present invention to provide a composition and method of preparation and method of application which is easy to prepare (formulate) and use (apply), and which is erodible (biodegradable) and safe to the environment, but which is effective for use in controlling one or more immature and mature stages of terrestrial insects or pests, particularly, but not exclusively, insects, and other arthropod pests.

It is a further object of the present invention to provide an agglomerated or nonagglomerated composition, encapsulated or non-encapsulated within a water soluble/degradable pouch, and methods of preparation and use which can incorporate a wide variety of potentially incompatible insecticidal or pesticidal ingredients into a single, stable and homogeneous solid or flowable delivery system to control a broad spectrum of terrestrial insect populations or other habitat-associated/related pests, in any target terrestrial habitat, and to provide for the variable time-release of the active ingredients.

Still another object of the present invention is to provide an agglomerated or non-agglomerated composition, a method for its preparation and a method for its application, which can incorporate a wide variety of insecticidal or pesticidal ingredients into a single, stable and non-homogeneous solid delivery system to control a broad spectrum of terrestrial insect populations or other habitat-associated/related pests, in any target terrestrial habitat, and to provide for the variable time-release of the active ingredients.

Still another object of the present invention is to provide a method for simultaneously or concurrently controlling two or more natural populations of terrestrial insects and habitat-associated terrestrial pests such as mites, fungi, weeds, nematodes, birds, rodents, etc., with a single, variable-density or variable-viscosity, insecticidal/pesticidal superabsorbent polymer carrier or matrix delivery formulation.

Still another specific object of the present invention is the provision of incorporating one or more surface-active/film-forming agents, surfactant(s) or oil(s) into a solid (encapsulated or not encapsulated within a water soluble pouch) or into a stable and homogeneous, variable-viscosity, flowable insecticidal, pesticidal or insecticidal/pesticidal superabsorbent polymer(s) formulation, the addition of which can slow the rate of release of one or more active ingredients from the delivery composition.

Still another specific object of the present invention is to provide a method for simultaneously or concurrently controlling two or more natural populations of terrestrial insects and/or habitat-associated/related pests that allows for broadcast coverage with a variety of solid or flowable superabsorbent polymer formulations with conventional application methods without significant losses to wind drift, while enhancing canopy penetration or target substrate adherence, and providing the active ingredient(s) and/or polymer matrix with increased resistance to degradation from ultra-voilet radiation (UV), volatilization, humidity, diffusion, microbial attack, temperature fluctuations, oxidation, seepage, run-off, etc., even after periods of wetting and drying.

These and other objects are accomplished by the compositions and methods of the present invention.

SUMMARY OF THE INVENTION

The use of superabsorbent polymer(s) of the present invention provides simple and easy techniques for the incorporation or encapsulation of a variety of insecticidal, pesticidal, and insecticidal/pesticidal ingredients, with or without other additives such as baits, into agglomerated solid carrier matrices, e.g., dense pellets, granules, water soluble pouches, or briquets, for the slow or controlled release of active agents in a variety of terrestrial habitats.

Agglomerated or non-agglomerated superabsorbent polymer formulations of the present invention containing one or more diluent or adjuvant surface-active/film-forming agents, surfactant(s) or oil(s) (such as oil baits), can effect a mechanism for reducing the rate of water absorption (hence superabsorbent polymer swelling), and thereby slow down the rate of release of one or more active agent(s) from the solid matrices, and extend the field life or persistence of the active agent(s) for a period of time greater than would be expected with superabsorbent polymer formulations containing no surfactant(s) or oil(s). In addition, agglomerated compositions can impart increased resistance to the active agents encapsulated within the matrix to environmental degradation due to ultra-violet radiation (UV), volatilization humidity, diffusion, microbial attack, temperature effects, oxidation, seepage, run-off, etc. Similarly, certain flowable, variable-viscosity superabsorbent polymer compositions of the present invention formulated with one or more surface-active/film-forming agents, surfactant(s) or oil(s), with or without water can slow or control the release rate of the active formulation ingredients, while enhancing target substrate adherence and minimizing wind drift loss.

The solid or flowable compositions of superabsorbent polymer(s) will be suitable with various insecticidal agent(s), and/or pesticidal agent(s) or other additive(s) which can be directly or indirectly placed in desired terrestrial habitat locations (e.g., indoor or outdoor) based on the type(s) of active ingredient(s), formulation(s), and insect or pest specie(s) to be controlled. In general, the superabsorbent polymer carrier/diluent-/encapsulation matrix, particularly when formulated with certain surface-active/film-forming agents, surfactants or oils, facilitates resistance to surface/subsurface run-off or percolation losses of active agents, and can provide active agent and/or matrix protection from environmental degradation due to UV, volatilization, oxidation, humidity, microbial attack, temperature fluctuation, etc., even after periods of wetting and drying. In addition, variable-viscosity sprayable, pumpable, or injectable formulations of superabsorbent polymer(s), water, and one or more surface-active/film-forming agent(s), surfactant(s) or oil(s), can effect a similar mechanism for variable time-release (i.e., slow or controlled release) of active ingredients in these compositions, thereby extending the field life or persistence of the polymer(s) insecticide(s), and/or pesticides, for a greater period of time than would be expected with superabsorbent polymer formulations containing no surface-active/film-forming agent(s), surfactant(s) or oil(s). This can extend the field persistence of the active agent(s) in the superabsorbent polymer formulation, and thereby assure that the frequency of costly insecticidal or pesticidal retreatments per habitat will be reduced.

The invention has found particular application as an insecticidal carrier agent, applied as a baited composition, particularly for ants for translocation into the pest habitat, (e.g. mound) typically by the foraging insect. (e.g. imported fire ants). The composition applied as a powder, granule, or agglomerate e.g., has the potential for dual physical/insecticidal dynamic behavior which enhances the effectiveness and activity of the active agent.

SPECIFIC ASPECTS

In accordance with the invention, an agglomerated or non-agglomerated solid (encapsulated or not encapsulated within a water soluble pouch) or variable-viscosity, flowable (aqueous or oil base) insecticidal delivery composition is provided for controlling populations of terrestrial insects, the delivery composition being applied by ground or aerial techniques (i.e., by aircraft, trucks, etc.) to a variety of terrestrial (i.e., non-aquatic) habitats. The compositions include at least one superabsorbent polymer, and at least one insecticidal agent, alone or in combination with water or oil, adjuvant(s), diluent(s), or carrier agent(s), or other additive(s), the superabsorbent polymer(s) and insecticidal agent(s) being present in a total amount effective to control the population of terrestrial insects. The diluent(s), adjuvant(s), carrier agent(s), or other additive(s), if present, is at a concentration adapted to improve formulation component mixing, compatability, and, or stability and/or to allow proper impregnation or mixing of the insecticidal agent(s) on, and/or in the superabsorbent polymer(s). Insecticidal agents for the control of adult and/or immature development stages are selected from solid and/or liquid insecticides, ovicides, larvicides, pupicides, conventional toxicants, chemosterilants, fumigants, systemics, pheromones, attractants, insect growth regulators, repellents, biological control agents, microbial control agents, pathogens, parasites, and mixtures thereof.

Further, in accordance with the present invention, a solid or flowable, variable time-release insecticidal delivery composition is provided for controlling a population of terrestrial insects, which includes one or more superabsorbent polymer(s) and mixture thereof, at least one insecticidal agent and at least one insecticidal adjuvant, carrier or diluent, the superabsorbent polymer, insecticidal agent(s), and adjuvant(s), carrier(s) or diluent(s) being present in a total amount effective to control a population of terrestrial insects, the variable time-release delivery composition being applied as a ground or aerial treatment to a variety of natural or artificial terrestrial (i.e., non-aquatic) habitats. Carrier, adjuvant, or diluent materials are selected from surfactants, alcohols, film-forming agents, surface-active agents, petroleum-or vegetable-and/or animal-base oils (e.g., an baits), etc., and mixtures thereof, the carrier, adjuvant, or diluent being present at a concentration required to slow, control or vary the rate of release or active components in the solid or flowable superabsorbent polymer composition.

In another aspect of the present invention, an agglomerated or nonagglomerated solid (encapsulated or not encapsulated within a water soluble pouch) or variable-viscosity, flowable pesticidal delivery composition is provided for controlling populations of terrestrial pests, the delivery composition being applied by ground or aerial techniques (i.e., by aircraft, trucks, etc.) to a variety of terrestrial (i.e., non-aquatic) habitats. The compositions include at least one superabsorbent polymer, and at least one pesticidal agent, alone or in combination with water or oil, adjuvant(s), diluent(s), or carrier agent(s), or other additive(s), the superabsorbent polymer(s) and pesticidal agent(s) being present in a total amount effective to control the population of non-insect terrestrial pests. The diluent(s), adjuvant(s), carrier agent(s), or other additive(s), if present, are at a concentration adapted to improve formulation component mixing, compatability, and/or stability and/or to allow proper impregnation or mixing of the pesticidal agent(s) on, and/or in the superabsorbent polymer(s). Pesticidal agents are selected from solid and/or liquid pesticides, acaricides,, miticides, nematicides, herbicides, hormones, sterilants, avicides, rodenticides, molluscicides, predicides, bactericides, or fungicides, and mixtures thereof.

As a further aspect of the present invention, a solid or flowable, variable time-release pesticidal delivery composition is provided for controlling a population of terrestrial pests which includes one or more superabsorbent polymer(s) and mixture thereof, at least one pesticidal agent and at least one pesticidal adjuvant, carrier or diluent, the superabsorbent polymer, pesticidal agent(s), and adjuvant(s), carrier(s), or diluent(s) being present in a total amount effective to control a population of terrestrial pests, the variable time-release delivery composition being applied as a ground or aerial treatment to a variety of natural or artificial terrestrial (i.e., non-aquatic) habitats. Carrier, adjuvant, or diluent materials are selected from surfactants, alcohols, film-forming agents, surface-active agents, petroleum-or vegetable-base oils, etc., and mixtures thereof, the carrier, adjuvant, or diluent being present at a concentration required to slow, control or vary the rate of release of active components in the solid or flowable superabsorbent polymer composition.

In yet another more detailed aspect of the present invention, there is provided a joint- or multi-action solid (encapsulated or not encapsulated within a water soluble pouch) or flowable, variable time-release insecticidal/pesticidal delivery composition for controlling a population of terrestrial environment insects and habitat-associated/related pests. The composition includes at least one superabsorbent polymer, at least one insecticidal agent, and at least one additional pesticidal agent (i.e., if the insecticidal agent does not have additional pesticidal applications), with or without water, oil or additional nontoxic adjuvants, diluents, or other additives. Diluent, adjuvants, or other additive ingredients are selected from surfactants, surface-active agents, film-forming agents, petroleum oils, vegetable oils, penetrants, spreading agents, suspending agents, wetting agents, stabilizing agents, compatability agents, sticking agents, carriers, binders, co-solvents, coupling agents, deflocculating agents, dispersing agents, waxes, oils, synthetic plastics, foams, anti-foaming agents, synergists, elastomers, natural or synthetic polymers, and other additives and mixtures thereof. The superabsorbent polymer(s), insecticidal agent(s), and additional pesticidal agent(s) and adjuvant(s) or diluent(s) are present in a total amount effective to simultaneously or concurrently control the population of terrestrial insects and habitat-associated/related pests, the variable time-release delivery composition being applied as a ground or aerial treatment to the target terrestrial habitat.

In accordance with another aspect of the present invention, there is provided a method for controlling a population of terrestrial environment insects or pests which includes the steps of:

preparing or formulating an agglomerated or nonagglomerated solid or flowable, insecticidal or pesticidal delivery composition which includes at least one superabsorbent polymer and at least one insecticidal or pesticidal agent, with or without water or oil, or additional nontoxic adjuvants, diluents, carriers or other additives, by a series of soakings, washes, variable speed blendings, salt/electrolyte conditioning treatments or reactions, and/or temperature and moisture conditioning treatments or reactions;

applying said insecticidal or pesticidal delivery composition in an amount effective to control a population of terrestrial insects or pests, the delivery composition being applied by ground or aerial treatment to the desired terrestrial habitat.

In accordance with still another aspect of the present invention, there is provided a method for simultaneously or concurrently controlling a population of terrestrial insects and habitat-related pests. The method includes the steps of:

preparing or formulating an agglomerated or nonagglomerated solid or flowable, variable-viscosity insecticidal/pesticidal delivery composition which includes at least one superabsorbent polymer, at least one insecticidal agent with or without water or oil, and with at least one additional pesticidal agent (i.e., if the insecticidal agent does not have additional pesticidal applications) and/or nontoxic diluent, adjuvant, carrier, or additive agent by a series of soakings, washes, variable speed blending, salt/electrolyte conditioning treatments or reactions, and/or temperature and moisture conditioning treatments or reactions; and applying said insecticidal/pesticidal delivery composition in an amount effective to simultaneously or concurrently control one or more populations of terrestrial environment insects and one or more populations of habitat-related pests (e.g., nematodes, mites, fungi, weeds, snails), with the delivery composition being applied by ground or aerial treatment to the terrestrial habitat.

A particular preferred advantageous application for the above insecticidal/pesticidal delivery composition(s) is against ants (e.g., fire ants) and other similar habitat-related pests. The invention composition can readily incorporate oil-based baits and compatible and non-compatible active agents and/or adjuvants. The superabsorbent polymers, although not effective as pesticides in and of themselves, effectively enhances the activity of the active agent. This could be partially due to the extremely hydrodynamic behavior of the superabsorbent polymer. For example, a conventional baited insecticide carrier foraged and brought into an ant colony or mound could require the ants to continually ingest or contact the baited hydrodynamically inactive carrier. With superabsorbent polymers, the extremely hydrodynamic behavior of the matrix will enable the polymer to intermittently swell and reswell within the colonies, hence simultaneously increasing worker contact/activity, the surface area of the matrix, and hence its presence (persistence) in the colony, and the active-agent release rate of the carrier matrix. The extremely hydrophilic nature of the polymer enhances this process even absent of direct wetting, by enabling swelling by preferential absorption of surrounding subsurface moisture.

The superabsorbent polymers of the present invention are synthetic organic polymers, which are solid and hydrophilic, absorbing over 100 times their weight in water. These superabsorbent polymers are substantially water insoluble, and can be acrylamide and acrylate polymers, co-polymers and ter-polymers which are optionally crosslinked or grafted. These superabsorbent polymers are typically in a powder, crystal, extruded, or flake form, adapted to be blended and/or agglomerated into an desired shape or form. The superabsorbent polymers may be, for example, acrylamide alkali metal acrylate co-polymers; propenenitrile homo-polymers, hydrolyzed alkali metal salts; polymers of propenamide and propenoic acid, alkali metal salts; hydrolyzed acrylonitrile co-polymers and starch graft co-polymers and ter-polymers thereof. All of these are designed to be hydrophilic, absorbing over 100 times their weight in water.

The solid or flowable superabsorbent polymer formulations of the present invention may be composed of one or more of a wide choice of solid and/or liquid insecticidal agents, such as insecticides, larvicides, pupicides, ovicides, hormones, insect growth regulators, biological control agents, microbial control agents, pathogens, parasites, conventional toxicants, fumigants, systemics, pheromones, repellents, chemosterilants, attractants, and/or one or more pesticidal agents such as miticides, acaricides, herbicides, hormones, molluscicides, sterilants, growth regulators, rodenticides, avicides, fungicides, bactericides, or predicides, and with or without nontoxic agents such as surfactants, spreading agents, fertilizers, adjuvants, carriers, binders, deflocculating agents, dispersing agents, synergists, penetrants, suspending agents, baits, sticking agents, wetting agents, stabilizing agents, compatability agents, co-solvents, coupling agents, foams, anti-foaming agents, diluents, waxes, oils, synthetic plastics, elastomers, inverting oils, natural or artificial polymers, and other additives and mixtures thereof; depending on the type or nature of the terrestrial habitat to be controlled, the environmental impact, and/or the developmental stage(s) and/or insect and/or pest specie(s) to be controlled. The solid or flowable formulations of the present invention are biodegradable. They are also storage stable when formulated, basically as stable as the individual components; however, increased stability may occur in solid matrix form over the flowable form. Solid or flowable superabsorbent polymer formulations of the present invention can take a wide variety of shapes, forms, and consistencies which may be required for a particular application. The solid or flowable superabsorbent polymer formulations of the present invention can have a variable time-release, either quick, or gradual as the situation requires. The present invention provides a superabsorbent polymer carrier, suspending, compatability, formulating, protective or encapsulation agent for the variable time-release or delivery of joint- or multiple-action formulations of liquid and/or solid insecticidal, pesticidal, and insecticidal/pesticidal agents that would otherwise be difficult or impossible to combine or mix as technical, oil-base, or water-base products into a homogeneous or non-homogeneous solid or homogeneous flowable formulation.

Solid or flowable insecticidal superabsorbent polymer bait or non-bait formulations of the present invention can be used to control terrestrial (non-aquatic) insects in any type of infested terrestrial area requiring control treatment. If necessary, solid or flowable insecticidal superabsorbent polymer formulations of the present invention can also be combined with additional pesticides to simultaneously or concurrently control terrestrial insects and habitat-related/associated pests such as mites, nematodes, weeds, fungi, rodents, etc., in a variety of terrestrial habitats that contain the target insect(s) or pest(s) (direct treatment) or that will eventually contain the target insect(s) or pest(s) (pretreatment). The solid water-activated hydrodynamic compositions have the ability to revert back to a dry state form and return to a wet release form and back again, depending on the habitat and/or climatological temperature/moisture/UV conditions. This ability to transform from a water-activated release form to an encapsulated dry or moist inactive, semi-active, static, or bait form that can help protect the active agents from environmental degradation (e.g., from UV, volatilization, microbial attack, temperature fluctuations, oxidation, diffusion, etc.) and back again (hence variable time-release), is a distinct advantage of the instant invention. This transformation/retransformation ability can also be found in the flowable compositions; however, to a lesser degree.

Compaction or agglomeration of the superabsorbent polymer matrix has been shown to effect a slow or controlled release mechanism for certain active ingredients. In addition, varying the ratio of different types of these superabsorbent polymers, that have differential water uptake or swelling characteristics (e.g., Super Sorb, Aqua Keep®, Water Lock®, Aridall®, and Aquastore® products), in a single compacted or agglomerated matrix may effect a mechanism to further enhance the slow release of certain active insecticidal, pesticidal, or insecticidal/pesticidal ingredients. The utilization of homogeneous (uniformly distributed ingredients) or non-homogeneous (layered ingredients) incorporation of two or more active agents into the solid composition composed of two or more polymers can also be used to vary the release rate and sequence of delivery into a desired habitat. The utilization of non-homogeneous solid compositions (i.e., active ingredients and/or polymers not uniformly distributed throughout matrix compositions) containing layers or stratifications of one or more active agents and/or superabsorbent polymers in a position or location for desired sequential release of active components from the solid matrix are possible. Active insecticidal and/or pesticidal agents can be formulated (i.e., layered) into a pellet from the central core to the periphery by disc pelletizing techniques.

Additional controlled release modifications can be obtained by the encapsulation of solid agglomerated or non-agglomerated compositions within walls (e.g., a pouch) composed of at least one water-soluble and/or biodegradable material selected from the group consisting of polyvinyl alcohol, polyethylene oxide and hydroxypropyl methyl cellulose, with or without cellulosic or paper laminates. Furthermore, the addition of adjuvants, carriers, or diluents such as surface-active/-film-forming agents, oils or surfactants to the insecticidal, pesticidal, or insecticidal/pesticidal formulation can further provide a mechanism to control (i.e., slow) the rate of release of the active ingredients. This advantage is particularly unique due to the relative ease of incorporation, and capacity of the superabsorbent hydrophilic polymer formulations for the mainly hydrophobic release controlling agents. As these hydrophobic agents can also have particular application as active agents the functions of controlled release variability can be joined with activity. Release of active insecticidal/-pesticidal ingredients into a terrestrial environment can also be affected by the degree of polymer matrix degradation due to ultra-violet radiation, microbial decomposition, PH etc. Surface-active/film-forming agents, oils or surfactants can also retard environmental degradation of the polymer matrix.

DESCRIPTION OF PREFERRED EMBODIMENTS

Surprisingly, it has been found that certain superabsorbent polymers constitute a novel class of chemicals useful as insecticidal/pesticidal delivery compositions for controlling populations of adult and immature insects and/or pests in a terrestrial environment area needing terrestrial insect/pest control treatment.

An insecticidal/pesticidal delivery composition is any composition which can carry, or be adapted to carry, insecticidal agent(s), pesticidal agent(s) or insecticidal and pesticidal agent(s), to the target habitat, natural or artificial, indoor or outdoor. The insecticidal/pesticidal delivery agent matrix for incorporation into solid or flowable compositions is broadly one or more superabsorbent polymers. Superabsorbent polymers, including starch graft co-polymers, are known in the art. See, for example, those described in U.S. Pat. Nos. 4,375,535 and 4,497,930 (incorporated herein by reference), which have disclosed uses as adhesives, flocculants, sizes, water-retaining materials for agriculture and water-absorbing materials for sanitary materials. However, the spectrum of advantages attendant the use of superabsorbent polymers in solid and flowable terrestrial insecticidal, pesticidal or insecticidal/pesticidal delivery compositions have gone unrecognized.

The superabsorbent polymers of the present invention are synthetic organic polymers which are solid and hydrophilic, absorbing over 100 times their weight in water. These superabsorbent polymers are typically in a powder, granule, extruded, or flake form, adapted to be blended and/or agglomerated into any shape or form.

The superabsorbent polymers may be, for example, acrylamide alkali metal acrylate co-polymers; propenenitrile homo-polymers, hydrolyzed, alkali metal salts; polymers of propenamide and propenoic acid, alkali metal salts; hydrolyzed acrylonitrile co-polymers, and starch graft co-polymers and ter-polymers thereof. All of these are designed to be hydrophilic, absorbing over 100 times their weight in water. The resulting hydrophilic polymers can absorb from over one hundred to greater than about 5000, more typically around 500 to about 1,000, times their own weight in water (measured using distilled water, pH 7.5, 25° C., 760 mm Hg. absorption within about 30 seconds). However, the absorption or swelling capacity and absorption or swelling time typically varies with each specific superabsorbent polymer.

One class of superabsorbent polymers include combinations of a starch and organic monomers, oligomers, polymers, co-polymers or ter-polymers. They may be manufactured in a variety of ways, for example, the methods described in U.S. Pat. Nos. 4,375,535 and 4,497,930, and can be, for example, the product of grafting corn starch (amylopectin) with acrylonitrile (an acrylic monomer or oligomer). A second class of superabsorbent polymers includes combinations of acrylamide and acrylate polymers, co-polymers and ter-polymers.

The superabsorbent polymers can also be propenoic or acrylonitrile/acrylamide-base polymers or co-polymers or ter-polymers that also show superabsorbency properties.

It has also been observed that superabsorbent polymers alone, or impregnated, mixed or combined with one or more insecticidal and/or pesticidal agent(s), with or without water or oil, or other additives have the ability to swell when in contact with water and release the impregnated substance(s) at rates that will vary with the type of solid or flowable formulation utilized. Superabsorbent polymers also have the ability under certain conditions to reform or contract to a congealed or crystal-like consistency similar to their original form when evaporation has caused the water to be removed from the sol, gels or gelly-like matrix, and then swell or regel when additional water is added. This ability to resume a functional or semifunctional active-agent, encapsulated release form after repetitive periods of wetting and drying in certain situations is advantageous for pretreatment and/or prolonged control release applications of solid or flowable insecticidal, pesticidal, or insecticidal/pesticidal formulations. Specifically, it has been found that when the superabsorbent polymer is impregnated or mixed with a surface-active/film-forming agent(s), surfactant or oil, water will be absorbed at a slower rate, thereby indicating that active agents in the solid matrix or flowable matrix formulations will be differentially released at slower rates than would be expected with formulations containing no surface-active/film-forming agents, oils or surfactants. Also, environmental decomposition of the polymer matrix from UV, microbial decomposition, etc., will be slower than matrices containing no surface-active/film-forming agent, surfactant or oils.

Non-limiting specific examples of superabsorbent polymers with differential swelling properties, and which are particularly useful in solid or flowable insecticidal, pesticidal, or insecticidal/pesticidal delivery formulations include:

(1) a co-polymer of acrylamide sodium acrylate (Terra-Sorb GB);
(2) hydrolyzed starch-polyacrylonitrile (Terra-Sorb);
(3) 2-propenenitrile, homo-polymer, hydrolyzed, sodium salt or poly (acrylamide-co-sodium acrylate) or poly (2-propenamide-co-2-propenoic acid, sodium salt), (Water Lock ® Superabsorbent Polymer G-100);
(4) starch-g-poly (2-propenamide-co-2-propenoic acid, sodium salt), (Water Lock ® Superabsorbent Polymer A-100);
(5) starch-g-poly (2-propenamide-co-2-propenoic acid,
(6) starch-g-poly (2-propenamide-co-2-propenoic acid, mixed sodium and aluminum salt), (Water Lock ® Superaborbent Polymer A-222) Sodium salt), (Water Lock ® Superabsorbent Polymer A-200);
(7) starch-g-poly (2-propenamide-co-2-propenoic acid, potassium salt), (Water Lock ® Superabsorbent Polymer B-204);
(8) poly (2-propenamide-co-2-propenoic acid, sodium salt), (Water Lock ® Superabsorbent Polymer G-400);
(9) poly-2-propenoic acid, sodium salt (Water Lock ® Superabsorbent Polymer J-500 or Aqua Keep ® J-500);
(10) sodium polyacrylate superabsorbent polymers (Aqua Keep ® J-400 and J-550);
(11) starch g-poly (acrylonitrile) or starch-g-poly acrylamide-co-sodium acrylate), (General Mills SGP ®5025);
(12) starch acrylonitrile co-polymer (Super Sorb/AG Sorbent);
(13) cross-linked modified polyacrylamides (Aquastore ® and Aquastore ®F);
(14) cellulosic laminates of poly-2-propenoic acid, sodium salt (Water Lock ® Superabsorbent Laminates L-413, L-415, L-425, L-435, or L-513); and
(15) cross-linked acrylics (Aridall ® 1078, 1080, 1091, 1125, 1092, or 1098).

Superabsorbent polymers are generally nontoxic biodegradable, and relatively inexpensive to buy or produce.

Insecticide and commercial formulations of these materials that may find application in the present solid or flowable insecticidal delivery compositions include cyclo compounds; carbamates; animal plant derivatives, synthetic pyrethroids, and inorganic compounds; diphenyl compounds and other nonphosphate insecticides; organophosphates-phosphoric acid prototypes; organophosphates-thiophosphoric acid prototypes; and organophosphates - dithiophosphate prototypes. Specific insecticides and formulations of these materials, the terrestrial insects that they control, effective application rates, toxicity, etc., are discussed by W.T. Thomson, 1985, in *Agricultural Chemicals, Book I Insecticides 1986–86 Revision*, Thomson Publications, Fresno, Calif., 255 pp.

Surfactants, film-forming/surface-active agents, or oils, useful in solid or flowable formulations of the present invention as carriers, diluents, adjuvants, release rate modifiers, etc., are generally organic chemicals that are soluble to essentially insoluble in water. They are generally nonionic, nonvolatile and can be liquid, semi-solid, or solid; however, they can be anionic or cationic, if necessary. They may have a low freezing point and a boiling point above the maximum air temperature of the environment into which they are placed. Examples of liquid, semisolid, or solid surfactants or film-forming or surface-active agents useful in conjunction with the present invention are the organic chemicals described in U.S. Pat. No. 4,160,033, which is herein incorporated by reference. Film-forming agents, surfactants, or alcohols such as 2-propanol, tridecyl alcohol, 2-ethyl butanol, 2-ethyl hexanol, 1-hexanol, acetone, xylene, decyl alcohol, polyoxyethylene (20) sorbitan trioleate, polyoxyethylene alkyl aryl ether, polyoxyethylene (5) sorbitan monooleate, isostearyl alcohol containing 10 oxyethylene groups, Morwet ® surfactants, isostearyl alcohol containing 20 oxyethylene groups; cetyl alcohol; stearyl alcohol; or petroleum-base oils such as mineral oils, diesel oils, etc., and mixtures thereof may also be used.

Various other exemplary surfactants include higher fatty acids, higher alcohol sulfate, alkyl aryl sulfonates, polyoxyethylene alkyl phenol ether, polyoxyethylene alkylamine, polyoxyethylene aklylamide, poly(oxyethylene-oxypropylene) co-polymer and polyoxyethylene-polyoxypropylene alkylene diamine alkyl trimethyl ammonium salt, alkyldimethyl benzylammonium salt, alkylpryidinium salt, alkyl betaine or alkyl imidazoline sulfonate.

Water soluble and/or degradable films or materials useful in the fabrication of pouches, bags, walls, containers, etc., for the encapsulation of solid agglomerated or non-agglomerated insecticidal, pesticidal, or insecticidal/pesticidal compositions are selected from the group consisting of polyvinyl alcohol, polyethylene oxide, and hydroxypropyl methyl cellulose, with or without cellulosic or paper laminates.

An insecticidal material is any chemical, agent, substance, or mixture thereof, used to control or kill adult or immature stages of insects in a variety of terrestrial (non-aquatic) habitats. Exemplary insecticidal materials can include insecticides, ovicides, larvicides, pupicides, adulticides, biological control agents, microbial control agents, hormones, pathogens, parasites, insect growth regulators, conventional toxicants, fumigants, systemics, chemosterilants, pheromones, attractants, repellents, surface-active agents, or petroleum or non-petroleum oils. Some insecticidal agents can have additional pesticidal applications.

A pesticidal material is any agent, substance, chemical, or mixture thereof used to control or kill adult or immature stages of non-insect pests in a variety of terrestrial (non-aquatic) habitats. Exemplary pesticidal materials can include nematicides, miticides, acaricides, herbicides, hormones, sterilants, molluscicides, growth regulators, rodenticides, fungicides, bactericides, avicides, or predicides. Some pesticides can have additional insecticidal applications.

Insecticidal compositions of the present invention are specifically directed against species of insects in the Orders Orthoptera, Thysanura, Dermaptera, Isoptera, Psocoptera, Mallophaga, Anoplura, Thysanoptera, Coleoptera, Hemiptera, Homoptera, Lepidoptera, Diptera, Siphonaptera, Hymenoptera, and Collembola. Pesticidal compositions of the present invention can be directed against species of the Class Arachnida, Class Nematoda, Class Gastropoda, Order Rodentia, Class Aves, Family Talpidae, Family Sciuridae, Order Chiroptera, Suborder Serpentes, Class Diplopoda, Class Chilopoda, Class Crustacea, and the Myceteae.

Insecticidal and pesticidal agents or formulations (i.e., insecticides, pupicides, larvicides, miticides, avicides, nematicides, insect growth regulators, repellents, attractants, fumigants, pathogens, rodenticides, etc.) useful in the present invention, and the insects or pests that they control are discussed in W.T. Thomas, 1985, *Agricultural Chemicals, Book I Insecticides*, 1985–86 Revision, Thomas Publications, Fresno, Calif., pp. 1–255, in George O. Poinar, Jr. and Gerald M. Thomas, 1978, *Diaonostic Manual for the Identification of Insect Pathooens*, Plenum Press, New York, pp. 1–218, in W.T. Thomas, 1986, *Agricultural Chemicals, Book III—Fumigants, Growth Regulators, Repellents and Rodenticides*, 1986 Revision, Thomas Publications, Fresno, Calif., 187 pp, in George W. Ware, 1980, *Complete Guide to Pest Control With and Without Chemicals*, Thomson Publications, Fresno, Calif., 290 pp., in W.T. Thomson,1986, *Acricultural Chemicals, Book II Herbicides*, 1986–87 Revision, Thomson Publications, Fresno Publications, Fresno, Calif., 301 pp., and in L.C. Truman and W.L. Butts, 1967, *Scientific Guide to Pest Control Operations*, Second Edition (Revised), Pest Control Magazine, Cleveland, Ohio, 187 pp.

Nontoxic adjuvant or diluent materials include water, carriers, baits, binders, fertilizers, deflocculating agents, penetrants, spreading agents, surface-active agents, surfactants, suspending agents, wetting agents, stabilizing agents, compatability agents, waxes, oils, inverting oils, co-solvents, coupling agents, foams, synergists, antifoaming agents, synthetic plastics, elastomers, natural or synthetic polymers, and other additives and mixtures thereof.

A proposed aqueous absorbency mechanism of acrylic-based superabsorbent polymers has been described by the Chemdal Corporation (Arlington Heights, Ill. 60004) in their Technical Data Sheets on Aridal ® Superabsorbent Polymers. The absorbency of acrylic-based superabsorbent polymers is attributed to carboxylic groups located on the backbone of the superabsorbent polymer. When natural (e.g., via rain, dew, metabolic or physiologic water) or artificial (e.g., via sprinklers, irrigation, etc.) water contacts the superabsorbent polymer, these groups solvate rapidly and develop mutually repulsive negative charges. This allegedly causes the superabsorbent polymer to uncoil and absorb many times its weight in water. Crosslinking prevents solution of the superabsorbent polymer. The aqueous medium rapidly becomes oriented on the surface of the superabsorbent polymer by virtue of hydrogen bonding. The resulting gel has remarkable ability to hold the aqueous medium even under pressure.

Superabsorbent polymers appear to hold fluids by a physico-chemical mechanism. Electrolytes/salts interfere somewhat with the hydrogen bonding and effect the absorbency. Crosslinked acrylic-based superabsorbent polymers always absorb less aqueous medium when electrolytes/salts are present.

When formulations are made by the addition of water or water-base insecticides, pesticides, or insecticide/pesticide compositions to various concentrations of superabsorbent polymers or vise versa, sols or gels of various consistencies (viscosities) or stiffnesses can form that may or may not be flowable. However, high shear mixing or the addition of various salts/electrolytes can break or interfere with the gel structure or hydrogen bonding, thereby producing flowable (e.g., sprayable) superabsorbent polymer insecticide, pesticide, or insecticide/pesticide aqueous formulations that have the desired viscosity. Viscosity modification will mainly be a function of the active and/or inactive formulation components, the water absorption characteristics of the superabsorbent polymer (i.e., the type and amount of superabsorbent polymers), shear time and strength used to mix the formulation and/or the concentration and type of salts/electrolytes used to modify the sol or gel consistency of the formulation. Therefore, the viscosity of the aqueous formulation containing one or more superabsorbent polymers can be altered to achieve optimum flowability, droplet size and quantity, and thereby improve the general ground or aerial application characteristics of the formulation for maximum control of the target insect or pest. Furthermore, active insecticidal or pesticidal ingredients encapsulated in the viscous/semi-viscous but flowable aqueous superabsorbent polymer formulation can be protected from degradation from the effects of ultraviolet radiation, volatilization, oxidation, temperature, microbial activity, evaporation, run-off, etc., particularly when used in solid compositions. Furthermore, evaporation of water from the flowable aqueous superabsorbent polymer/insecticide or pesticide formulation can result in a solid congealed-like insecticide/pesticide-encapsulated matrix, thereby protecting the active components for prolonged periods until release of the insecticidal, pesticidal, or insecticidal/pesticidal ingredient(s) is triggered by water, biodegradation, or when the formulation is eaten in bait form.

Water-activated and biodegradable superabsorbent polymers formulated into an agglomerated or nonagglomerated bait-control agent formulation can be removed from the application site by, e.g., foraging insects, and subsequently translocated to mounds or nests for feeding to caste members and broods and/or used as structural building components and integrated directly into the mound or nest where the active control agent will be released and retained in close association with the target population. This association is enhanced by the hydrodynamic nature of the superabsorbent formulation and its potentially persistent nature in association with the target habitat (i.e., mound or nest). Formulations of this type can be particularly useful in controlling insects such as red and black imported fire ants, mole crickets, grasshoppers, etc., or rodents such as rats and mice. Once ingested, internal release of active ingredients in polymer-based bait formulations will be dependent on the various physiological parameters of the target insect or pest, e.g., on the water, PH, and/or electrolyte concentration of the gut, and on digestion, absorption, and excretion rates.

Applications in the release of insecticidal or pesticidal agents from solid or flowable superabsorbent polymer compositions in personal protection devices and in veterinary medicine (e.g., insecticidal/repellent polymer-base creams, pastes, or solids can be incorporated into fabrics for use in repellent jackets, ear tags for livestock, or cat/dog flea and tick collars) are also proposed.

The incorporation of active insecticidal/pesticidal agents (e.g., residual) into rigid or extruded superabsorbent polymers for controlled release applications is also contemplated. For example, a coating of superabsorbent polymer and insecticidal agent could be dipped or sprayed on selected interior wooden structures to form a protective controlled release barrier against termite attack, as well as attack from other wood-destroying insects and fungi. The use of these formulations in other interior or exterior pest control applications (particularly in interior dwelling structures) may also be considered.

It is further contemplated that the superabsorbent polymer formulations in accordance with the invention can be used with or without insecticidal or pesticidal agents in an agglomerated or nonagglomerated form as a treatment or pretreatment for active pest breeding areas. For example, the superabsorbent polymer formulations with or without active agents can be used as a moisture/water management aid to reduce or eliminate water that is necessary for the area to become an active pest breeding ground. For example, wet and damp silage and manure are commonly breeding areas for immature stages of flies. As a further application of the present invention, it is contemplated that such areas would be treated directly or by use of injection techniques to rapidly remove water from the potential breeding areas. The composition will alter the breeding environment to make it unsuitable for that purpose while preventing the emergence of the adult forms of the immature stages already under development. As a treated medium area dries the polymer will promote the formation of a crust which can further inhibit ovipositing insects and the emergence of mature stages under development. This procedure can be used in a number of pest breeding areas requiring moist conditions such as silage, manure pits, etc.

Impregnation or mixing of superabsorbent polymers with fatty alcohols, film-forming agents, surface-active agents, surfactants, or hydrophobic oils appears to delay or slow down the rate of water absorption of superabsorbent polymers, thereby providing a useful mechanism for slow or controlled release of insecticidal, pesticidal or insecticidal/pesticidal agents in terrestrial environments. The slow or controlled release process could be further modified or delayed by the degree of compaction of the powdered, crystal, extruded, or flaked superabsorbent polymer/insecticidal, or superabsorbent polymer/insecticidal/pesticidal agent formulation, by varying the size of an orifice in a container into which the insecticidal or pesticidal delivery composition is placed, by varying the concentration of adjuvants or diluents such as film-forming agent(s), surface-active agent(s), surfactant(s), or oil(s), by varying the concentration of different types of superabsorbent polymers, by utilization of water soluble/degradable pouches, and/or by adding one or more binders. When the matrix is wetted, water (concentration dependent) is differentially held within the gel-like or variable-viscosity, sol-like superabsorbent polymer matrix at a stiffness or strength that is dependent on whether a solid or flowable formulation is used (i.e., the amount of water in the formulation), and therefore evaporates slower than an equivalent amount of superabsorbent polymer-free standing water. Furthermore, the addition of film-forming agents, surface-active agents, surfactants, or oils to the superabsorbent polymer (s) also appears to retard the rate of water loss. However, eventually the superabsorbent polymer will restore to a congealed or crystal-like state that can be similar to its initial condition when dry, with loss of active agent dependent on whether it is mixed in a surface-active/-film-forming agent, oil or surfactant, the type of superabsorbent polymers, the presence of additional additives or diluents, and/or on the climatological/habitat moisture/water, PH, UV, microbial activity, etc., to which the formulation is exposed. These observations further suggest additional field persistence mechanisms for variable time-release (controlled release) of any active insecticidal, or pesticidal, or insecticidal/pesticidal ingredients which are added to the solid or flowable superabsorbent polymer formulations.

It should be noted that certain electrolytes or salts (e.g., alkali metal halides such as sodium chloride, potassium chloride, sodium sulfite, etc.) have been shown to either break down the gel or sol superabsorbent polymer matrix when introduced into or exposed to water by interfering with hydrogen bonding. Various concentrations of one or more salts/electrolytes can be added separately or included as an integral part of the active ingredient in the insecticidal, pesticidal, or insecticidal/pesticidal formulation. This has an impact on the viscosity, swelling and/or water absorbency of superabsorbent polymers and subsequent population control ability of the insecticidal, pesticidal or insecticidal/pesticidal delivery compositions, i.e., the swelling or water absorbency (hence controllability) of the superabsorbent polymer will directly affect the release rate of certain insecticidal, pesticidal or insecticidal/pesticidal agents that are impregnated therewithin. Therefore, it is possible to utilize certain salts or electrolytes directly or indirectly in superabsorbent polymer-base solid and flowable insecticidal, pesticidal or insecticidal/pesticidal formulations as another mechanism to regulate the viscosity (i.e., flowability) of aqueous formulations and alter or control (i.e., slow down) the release rate of solid and flowable formulations. The salt content or PH of the terrestrial habitat when wetted may also have an effect on kill rate of the target species by affecting the solid or flowable superabsorbent polymer water absorbency, bonding, matrix swelling, breakdown, decomposition, and/or release of active insecticidal, pesticidal, or insecticidal/pesticidal ingredients. The addition of salts/electrolytes to the matrix formulation, in combination with salts/electrolytes in the terrestrial habitat, may also affect a mechanism to vary these factors The ability of the hydrophilic polymer to incorporate relatively large quantities of hydrophobic substances also renders the composition suitable for controlled slow release of such hydrophobic components. Such superabsorbant polymer compositions can be employed as a pest control active agent dispenser in enclosed areas and/or used with attractants to bring the pest toward the dispenser. The composition can also be used with suitable protective hydrophobic outer layer in a laminate, such as is disclosed in U.S. Pat. No. 4,160,335, the substance of which is incorporated by reference. The hydrophobic protective layer should allow migration of the active pest control agent but should protect the superabsorbant composition from the effects of moisture, which would activate the hydrodynamic characteristics of the composition. In areas where the composition is not likely to contact with water, the use of a protective hydropholic layer can be dispensed with and the composition used directly, such as in internal structural and functional materials. The composition can be extremely rigid when exposed to ordinary atmospheric moisture and could be used in drywall, insulation, paneling, ceiling tile, etc., without a hydropholic protective layer. The ease of incorporation and the broad spectrum of incorporable active agents makes the composition suitable for long-term formative protection of a broad spectrum of household pests. By incorporation of the superabsorbent polymer pest control composition into structural elements, it is possible to protect those inaccessable areas of a structure where pests are most likely to hide with a composition capable of both long term and broad spectrum effectiveness.

It should be noted that viscous/semi-viscous aqueous superabsorbent polymer compositions can be rendered flowable by the use of vigorous or high-shear mixing/agitation. Any suitable equipment or technique used to incorporate insecticides or pesticides into an aqueous emulsion a supension can be suitably used to render a non-flowable superabsorbent-based composition flowable. Inverting oil techniques are also appropriate for mixing and dispensing a highly viscous aqueous superabsorbent polymer composition composed of water, at least one insecticidal and/or pesticidal agent, film-forming agent or oil, and with or without pesticides and/or other additives. The degree of mixing/agitation of the superabsorbent polymer-base aqueous composition will also have an effect on the variable release rate characteristics of active agents by effecting (i.e., breaking or disrupting) the bonding of water with the superabsorbent polymer matrix.

The specific gravity of the delivery composition can also be adjusted by the use of solid or liquid surfactants, oils, surface-active or film-forming agents, water, alcohols, clays, talcs, encapsulation films, or fillers which can include viscosity modifiers and the like.

The water, surfactant, or oil-dissolved, suspended, or dispersed active agent can be incorporated into the superabsorbent polymer as an emulsion. This requires the use of suitable emulsifying agents to form a stable emulsion, however, an unstable emulsion may be preferred for certain applications. The emulsion can also be rendered somewhat ionic for example, by use of certain surfactants, to promote preferable ionic bonding with the superabsorbent polymers. Suitable emulsifiers such as ammonium lineolate, ethylene oxides adducts, acyl polyglycol ethers, oxyethylated fatty alcohols, alkali metal starches as discussed in U.S. Pat. No. 2,347,680, or starch propionates as disclosed in U.S. Pat. No. 4,059,458. However, any suitable known surfactant, surface-active agent, film-forming agent, or oil, can be employed.

The form of the solid delivery composition will be dependent on the particular contemplated application technique and target. Fine particulate or granula compositions are usually preferred for foraging insects, compositions of which are intended for use in their natural habitat (i.e., mound or nest). This can be accomplished by high-shear mixing, fine agglomeration techniques, etc. Suitably larger agglomerates or particles are desirable for larger targets such as rodents. These and other variations would be readily apparent to one of skill in the art based on the above disclosure and the particular need at hand.

The amount of active agent in the delivery composition will depend on the target insect or pest, the active insecticidal or pesticidal agent involved, the superabsorbent polymer, whether or not water is present, and whether any additional adjuvants and/or diluents are added. Generally, the weight ratio of superabsorbent polymer to insecticidal and/or pesticidal agent(s) and any additional diluent or adjuvant ingredient(s) is from about 0.1:100 to about 100:0.001, the insecticidal and/or pesticidal agent(s) being incorporated in the solid or flowable delivery composition for application at rates effective to control the target terrestrial insect and/or pest. The ratio of superabsorbent polymer(s) to any additive diluent or adjuvant such as a surfactant, oil, surface-active or film-forming agent(s) is from about 0.1:1 to about 100:0.01. The ratio of superabsorbent polymer to water in a flowable composition is generally 0.001:100 to 1:1

EXAMPLES 1-11

Bioassays and field evaluations were conducted to determine the efficacy of several solid or flowable superabsorbent polymer insecticidal bait and/or contact formulations in controlling several species of adult and immature terrestrial insects. Representative target terrestrial insects were the German cockroach *Blattella qermanica* (Table 1), the red imported fire ant *Solenopsis invicta* (Tables 2-3), crickets of the family *Gryllidae* (Tables 4-5), and the yellow mealworm *Tenebrio molitor* (Tables 6-7). Bioassays against cockroaches, crickets, and mealworms were conducted in quart mason jars with screened lids at ca. 80° F. (ambient), while fire ants were tested under natural field conditions.

Insecticides used in the superabsorbent polymer formulations were Fenoxycarb (Ethyl [2-p-phenoxyphenoxy)-ethyl]carbamate) or Dursban® 4E (0,0-Diethyl-0-(3,5,6-trichloro-2-pyridyl)phosphorothioate). Fenoxycarb (Dr. R. Maag Ltd., Dielsdorf, Switzerland) is a carbamate compound used as an insect growth regulator either by contact or as a stomach-poison. Fenoxycarb has been shown to be useful in controlling ants, cockroaches, fleas, ticks, chiggers, stored products insects, termites, spruce budworm, mosquitoes, gypsy moth, bollworms, cotton leaf perforator, pear psylla, scales, leafminers, and others. Dursban® (Dow Chemical Co., Midland, MI 48640) is an organic phosphate insecticide which acts primarily by contact activity and as a stomach-poison. Dursban® has been shown to be useful in controlling ants, aphids, boll weevil, bollworms, chinch bugs, cockroaches, corn borers, corn rootworm, crickets, cutworms, earwigs, grasshoppers, leafhoppers, mealybugs, mites, mosquitoes, peach tree borer, peach twig borer, scales, silverfish, spiders, thrips, ticks, tobacco budworms, webworms, whiteflies, white grubs, wireworms, and many others.

Superabsorbent polymers evaluated in the solid or flowable insecticidal formulations were Super Sorb, Water Lock® G-100, Water Lock® A-100, Water Lock® A-200, Water Lock® B-204, Water Lock®/Aqua Keep® J-500, Aquastor®, Aquastore® F, Aridall® 1078, Aridall® 1091, and/or Aridall® 1092.

Insecticides were mixed with or impregnated on/in superabsorbent polymers, with or without water, by vigorous handmixing or shaking (0.5-2 min), with a Fisher Dyna-Mix (Model 143) at 1,800 rpm (ca.0.5-1 min) and 2,400 rpm (ca. 2-3 min), and/or with a G.E. hand mixer (Model 420A) at low speed (ca. 2-3 min). The order of component mixing and the duration of mixing will be dependent on the type of superabsorbent polymers, the type of insecticidal or pesticidal ingredients used in the formulation, and/or the type of superabsorbent polymer formulation (i.e., solid or flowable).

Insecticides were formulated in the solid or flowable compositions for addition to the test chambers or natural habitats as a bait and/or contact formulation at rates recommended for the control of the target insect populations. Soybean oil or peanut oil was utilized as a diluent/bait in the superabsorbent polymer insecticidal formulations. Insecticidal compositions were placed in the target habitat as a bait or topically on the target insect.

The comparative rates of natural environmental degradation of powdered superabsorbent polymer-based compositions formulated with and without the 2 mol ethoxylate of isostearyl alcohol (Arosurf® 66-E2) or soybean oil (Table 8), and the subsequent active agent-/matrix stability/activity (Table 9) were determined on sandy soil/grassy field/pond conditions.

The active agent release potential of a variety of superabsorbent polymer-bait (soybean oil), formulations translocated by fire ant workers into ant mounds were determined in natural field conditions (Table 10). Fire ants were allowed to forage on 20 g of a polymer-bait formulation that was scattered around a mound. One soil core sample per mound was then taken ca. 11 days posttreatment with a PVC pipe (1¼ inch ID) by driving the pipe into the center of the mound down to a distance of ca. 12 inches. The core was then removed and six, ca. 2 inch samples were sequentially removed from the pipe beginning with the lowest depth and placed into a plastic cup of R.O. water (ca. 50 ml). Swelling was used to indicate polymer presence in the mound galleries or chambers and was used as the indicator for depth translocation and matrix stability and release potential.

EXAMPLE I

Results of bioassays concerning the comparative efficacy of solid superabsorbent polymer-base insecticidal compositions against nymphal stages of the German cockroach, *Blattella germanica* are presented in Table I. The data indicated that superabsorbent polymers can be used as the matrix for the creation of novel solid (or flowable) insecticide (fenoxycarb) bait formulations (contact or stomach poison) to provide control of cockroaches that are resistant to conventional organophosphate insecticides.

Fecal droppings throughout the test containers were observed to swell when a drop of water was added, thereby indicating the swelling activity and extended active agent release potential of the superabsorbent polymer bait formulations that had passed through the gastro-intestinal tract. Active superabsorbent polymer (i.e., swellable via the addition of water) was also recovered from the guts of dissected cockroaches that were fed on superabsorbent polymer compositions formulated with and without fenoxycarb. A drop of flowable semi-viscous compositions of several superabsorbent polymer-base fenoxycarb formulations applied to a dorso-thoracic area were observed to adhere to the cockroach cuticle and form a tiny dry crystalline patch or crystal-like formulation area 24-48 hr posttreatment. The addition of water to this area resulted in swelling of the polymer formulation, and thereby suggested the controlled release potential of various flowable superabsorbent polymer-base insecticide/pesticide formulations.

EXAMPLE II

Results or field trials (Table 2) against adult and immature stages of the red imported fire ant with several solid superabsorbent polymer-base fenoxycarb bait (soybean oil) formulations indicated that these solid bait formulations applied as powders or granules could be used to control natural populations of the imported fire ant. Observations of mounds that were treated with superabsorbent polymer-base bait compositions that were not formulated with fenoxycarb indicated that these formulations had no ant control potential.

EXAMPLE III

Data from additional trials (Table 3) against natural populations of the imported fire ant with solid superabsorbent or non-superabsorbent carrier matrices applied to the habitat in a powder or granular form, or in biodegradable/water soluble 2 mil polyvinyl alcohol (PVA) pouches (Polymer Films Inc., Rockville, Conn. 06066 or Mono-Sol Division, Chris Craft Industries Inc., Gary, Ind. 46043) indicated that effective control can be obtained with either type of application procedure. Foraging ants were observed within PVA pouches containing superabsorbent and non-superabsorbent formulations.

Matrix degradation observations over the 13 week test period reported in Table 3 suggested that superabsorbent polymer formulations remained more stable than zein (corn protein) formulations that were subjected to equivalent fluctuating environmental/climatological events (e.g., dew, rain, UV, microbial attack, etc.), and therefore could release, re-release, and/or protect the bioactive agent for a greater period of time than would be expected with non-superabsorbent polymer formulations. Additional comparative observations (Table 3) between superabsorbent and non-superabsorbent formulations encapsulated within PVA pouches indicated that enhanced field activity/stability/protection/persistence of the powdered or granular insecticidal formulation applied in PVA pouches could result, when subjected to adverse environmental/climatological pressures such as rain, UV, microbial attack, oxidation, etc. Non-fenoxycarb superabsorbent or non-superabsorbent matrix formulations encapsulated within PVA pouches were observed to have no insecticidal activity against natural fire ant populations.

EXAMPLE IV

Comparative bioassays against crickets (Table 4) with several solid superabsorbent polymer-based bait (peanut oil and potatoes) Dursban ® 4E formulations indicated that various superabsorbent polymers could be used in preparing effective insecticidal formulations for the control of adult and immature stages of crickets. Superabsorbent polymer formulations without Dursban ® had no insecticidal activity against crickets. However, active polymer (i.e., swellable on the introduction in water) was recovered in cricket fecal droppings as well as in the guts of dissected crickets that were exposed to polymer compositions with and without Dursban ®. Starch compositions appeared to be readily degraded/digested/water soluble, thereby indicating a poor biological/environmental persistence potential when compared to superabsorbent polymer formulations. This polymer stability suggested the potential for enhanced protection and prolonged release of insecticidal agents.

EXAMPLE V

Comparative bioassays against crickets with variable-viscosity, flowable (Table 5) superabsorbent polymer-based Dursban ® 4E bait/contact formulations indicated that effective cricket control could be obtained with these formulations. In general, the data indicated that superabsorbent polymer formulations generally kill faster than a formulation composed of non-superabsorbent materials (i.e., soluble starch). In addition, active polymer (i.e., swellable on exposure to water) was identified in fecal droppings, on hind torsal segments, lateral head regions, around the anal area, and in the gut of dissected specimens that were topically treated with both insecticidal and non-insecticidal formulations. All formulations were thoroughly cleaned (i.e., removed) from the topical application site. Evaporation of water from several flowable polymer formulations found on dead crickets over a 24–48 hr period resulted in scale, patch, or crystal-like areas that adhered to various cuticular body regions where the polymer formulations were translocated. The addition of water to these areas resulted in polymer swelling. Results suggested mechanisms for potential polymer-induced active agent protection and controlled release.

EXAMPLE VI

Comparative bioassays against larvae of the yellow mealworm (Table 6) with several solid superabsorbent polymer-based Dursban ® 4E bait formulations indicated that effective control of immature stages could be obtained with powdered or granular polymer compositions. Polymer compositions without Durban ® had no significant insecticidal activity. In general, superabsorbent polymer formulations killed faster than a non-superabsorbent polymer (soluble starch) formulation. Matrix stability of superabsorbent polymer formulations suggested controlled release potential for one or more active agents incorporated in the composition.

EXAMPLE VII

Comparative bioassays against larvae of the yellow mealworm with several flowable (Table 7) superabsorbent polymer-based Dursban ® 4E bait/contact formulations indicated that variable-viscosity polymer formulations could be used to control immature stages of the yellow mealworm. In general, a polymer-based formulations killed larvae faster than a non-superabsorbent polymer formulation. No insecticidal activity was observed in superabsorbent polymer compositions formulated without Dursban ®. Active polymer (i.e., swellable on exposure to water) was observed on leg, thoracic, and abdominal regions of dead mealworms. Patches of crusty or scale/crystal-like areas of dehydrated polymer formulations were observed firmly adhered to these exoskeletal areas 24–48 hrs posttreatment. Swelling of these polymer-based areas resulted upon introduction of the larvae to water, thereby suggesting the active agent encapsulation and controlled release potential of flowable superabsorbent polymer-based formulations.

EXAMPLES VIII–IX

Field evaluations concerning the comparative environmental persistence of technical and Arosurf ® 66-E2—or soybean oil—formulated superabsorbent polymers exposed to natural field conditions are presented in Table 8. Results indicated that a variety of polymer formulations containing Arosurf ® 66-E2 or soybean oil persisted in natural habitats subjected to rain, UV, microbial attack, oxidation, etc., significantly longer than technical polymers that were not formulated with these materials. In general, Arosurf ® 66-E2 appeared to protect Super Sorb significantly better than soybean oil; however, the Super Sorb-soybean formulation persisted in the field significantly longer than technical Super Sorb. The comparative stability of these environmentally stressed solid superabsorbent polymer formulations of Arosurf® 66-E2 are presented in Table 9. This data (Tables 8 and 9) suggests that various oils, surface-active agents, film-forming agents, or surfactants can be used as a superabsorbent polymer formulation ingredient that can act as an insecticide/pesticide diluent or bait and/or as a protective agent to stabilize the polymer matrices and active insecticidal/pesticidal agents, and thereby enhance the field life, persistence, and release of active agents in natural habitats for longer periods of time than would be expected with insecticide/pesticide formulations not containing oils, surfactants, surface-active agents, or film-forming agents.

EXAMPLE X

A series of field evaluations to determine the subsurface translocation of a variety of superabsorbent polymer-based bait (soybean oil) formulations by imported fire ant workers, and subsequent controlled release potential of these formulations are reported in Table 10. The data indicates that active polymers (i.e., water swellable), that have the capacity for active agent release were present in the galleries or chambers of fire ant mounds at 11 days posttreatment at varying depths. Observed variations and similarities in subsurface locations among mounds were presumed to be related to polymer types, mound sizes, ant populations, subsurface soil profiles, and/or to the sampling technique.

EXAMPLE XI

Observation during the course of field evaluations to determine the environmental persistence of several 20 g solid (powdered) superabsorbent polymer-base bait/-diluent compositions indicated that a formulation composed of Water Lock® A-100 (50%) and soybean oil (50%) was extremely attractive to a wild racoon. Observations of racoon tracks around samples of 50 and 100% eaten polymer formulations indicated the feeding preference/attractiveness of raccoons to superabsorbent polymer-base compositions, and suggested the use of superabsorbent polymer bait-predicide formulations to control unwanted predator populations.

TABLE 1

Efficacy of solid superabsorbent polymer-base fenoxycarb bait formulations against immature stages of the German cockroach *Blattella germanica*.[1]

| Test no. | Formulation ingredients per test chamber[2] (concentration) | No. nymphs[3] | Percentage reduction of nymphs at designated posttreatment interval (weeks)[4] 1 | 2 | 3 | 4 | 5 | 6 | 7 | 8 |
|---|---|---|---|---|---|---|---|---|---|---|
| 1a | Aqua Keep ® J-500 (50%) + fenoxycarb (0.5%) + peanut oil (48.5%) + rabbit chow (1%) | 25 | 0 | 0 | 0 | 0 | 32 | 60 | 64 | 64 |
| 1b | Aqua Keep ® J-500 (50%) + peanut oil (49%) + rabbit chow (1%) | 12 | 0 | 0 | 0 | 0 | 0 | 0 | 0 | 0 |
| 2a | Aqua Keep ® J-500 (50%) + fenoxycarb (0.05%) + peanut oil (48.5%) + rabbit chow (1%) | 26 | 0 | 0 | 0 | 0 | 15.4 | 61.5 | 96.1 | 96.1 |
| 2b | Aqua Keep ® J-500 (50%) + peanut oil (49%) + rabbit chow (1%) | 12 | 0 | 0 | 0 | 0 | 0 | 16.7 | 16.7 | 16.7 |
| 3a | Aridall ® 1092 (50%) + fenoxycarb (0.5%) + peanut oil (48.5%) + rabbit chow (1%) | 39 | 0 | 0 | 0 | 7.7 | 51.3 | 97.4 | 97.4 | 100 |
| 3b | Aridall ® 1092 (50%) + peanut oil (49%) + rabbit chow (1%) | 14 | 0 | 0 | 0 | 0 | 0 | 0 | 7.1 | 7.1 |
| 4a | Aridall ® 1092 (50%) + fenoxycarb (0.5%) + peanut oil (48.5%) + rabbit chow (1%) | 21 | 0 | 0 | 23.8 | 23.8 | 71.4 | 100 | — | — |
| 4b | Aridall ® 1092 (50%) + peanut oil (49%) + rabbit chow (1%) | 26 | 0 | 0 | 0 | 0 | 0 | 0 | — | — |

[1]Cockroaches are an organophosphate resistant strain reared at the Department of Entomology and Nematology, University of Florida, Gainesville, Florida. Non-fenoxycarb formulations considered as check/controls.
[2]Test chambers consisted of one quart glass mason jars with screened lids. Each test chamber contained 5 ml water on a 1 × 1 inch sponge and ca. 0.5 g polymer formulation in a 2 × 2 inch plastic weigh dish.
[3]Nymphs 1-5 days old at the time of testing. Formulation baits consisted of peanut oil (Sigma Chemical Company, St. Louis, MO 63178) and rabbit chow (Manna Pro ® Double Duty ®, Complete Rabbit Feed, Manna Pro Corporation, Tampa, FL 33601).
[4]Test terminated at 8 weeks at highest mortality indicated or when 100% test mortality was obtained.

TABLE 2

Efficacy of solid superabsorbent polymer-base fenoxycarb bait formulations against adult and immature stages of natural field populations of the red imported fire ant *Solenopsis invicta*.[1]

| Test no. (Mound ID) | Formulation ingredients (concentration) | Total formulation application rate per mound (g)[2] | Reduction of ant population per mound based on a qualitative observational scale of mound activity at indicated posttreatment intervals (weeks)[3] (Scale: 0 to 10; 0 = 100% inactive or dead, 5 = ca. 50% decline in population, 10 = 100% active). 1 | 2 | 3 | 4 | 5 | 6 | 7 | 8 | 9 |
|---|---|---|---|---|---|---|---|---|---|---|---|
| 2(A) | Super Sorb (87.5%) + fenoxycarb (1%) + Soybean oil (11.5%) | 20 | 10 | 10 | 9 | 7 | 5 | 5 | 5 | 5 | 3 |
| 2(B) | Aridall ® 1092 (75%) + fenoxycarb (1%) + Soybean oil (24%) | 20 | 10 | 10 | 10 | 9 | 9 | 9 | 6 | 5 | 5 |
| 2(C) | Aquastore ® (87.5%) + fenoxycarb (1%) + +Soybean oil (11.5%) | 20 | 10 | 10 | 10 | 7 | 6 | 5 | 5 | 3 | 3 |
| 2(D) | Aqua Keep ® J-500 (75%) + fenoxycarb (1%) + Soybean Oil (24%) | 20 | 10 | 10[4] | 7 | 7 | 5 | 5 | 5 | 5 | 3 |
| 2(E) | Super Sorb (87.5%) + Soybean oil (12.5%) | 20 | 10 | 10 | 10 | 10 | 10 | 10 | 10 | 10 | 10 |
| 2(F) | Aqua Keep ® J-500 (75%) + Soybean oil (25%) | 20 | 10 | 10 | 10 | 10 | 10 | 10 | 10 | 10 | 10 |

TABLE 2-continued

Efficacy of solid superabsorbent polymer-base fenoxycarb bait formulations against adult and immature stages of natural field populations of the red imported fire ant *Solenopsis invicta*.[1]

| Test no. (Mound ID) | Formulation ingredients (concentration) | Total formulation application rate per mound (g)[2] | Reduction of ant population per mound based on a qualitative observational scale of mound activity at indicated posttreatment intervals (weeks)[3] (Scale: 0 to 10; 0 = 100% inactive or dead, 5 = ca. 50% decline in population, 10 = 100% active). | | | | | | | | |
|---|---|---|---|---|---|---|---|---|---|---|---|
| | | | 1 | 2 | 3 | 4 | 5 | 6 | 7 | 8 | 9 |
| 2(G) | Control (no formulation) | — | 10 | 10 | 10 | 10 | 10 | 10 | 10 | 10 | 10 |

[1]Test sites are in Lee County, Florida, in sandy soil with grass around mound. Mound diameters ranged from ca. 6 × 7 to ca. 10 × 12 inches.
[2]Polymer formulations (ca. 98%) hand sprinkled around mound perimeter at a distance of ca. 2 ft. from mound; ca. 2% of each formulation applied directly on mound. Most of the polymer formulations (ca. 75–100%) removed by foraging workers and taken into mounds. Non-fenoxycarb polymer formulation considered as check/control. Formulation bait consisted of soybean oil (Sigma Chemical Company, St. Louis, MO 63178).
[3]Test terminated at 9 weeks posttreatment at highest mortality indicated. Dead and deformed ants found in all mounds treated with fenoxycarb. Rain (<1 to 1.64 inches) recorded in weeks 1–6 and 8.
[4]Polymer detected from soil obtained from a depth of ca. 8 inches below the mound.

TABLE 3

Efficacy of solid superabsorbent and non-superabsorbent matrix-base fenoxycarb bait formulations dispensed as a powder or in polyvinyl alcohol (PVA) pouches against adult and immature stages of natural populations of the red imported fire ant *Solenopsis invicta*.[1]

| Test no. (Mound ID) | Formulation ingredients (concentration) | Total polymer formulation application rate per mound (g)[2] | Reduction of ant population per mound based on a qualitative observational scale of mound activity at indicated posttreatment intervals (weeks)[3] (Scale 0 to 10; 0 = 100% inactive or dead, 5 = ca. 50% decline in population, 10 = 100% active). | | | |
|---|---|---|---|---|---|---|
| | | | 1 | 2 | 5 | 13 |
| 3(A) | Super Sorb (75%) + fenoxycarb (1%) + Soybean oil (24%) + PVA | 20 | 10 | 8 | 2 | 0 |
| 3(B) | Super Sorb (75%) + fenoxycarb (1%) + Soybean oil (24%) | 20 | 9 | 5 | 2 | 2 |
| 3(C) | Zein (75%) + fenoxycarb (1%) + Soybean oil (24%) + PVA | 20 | 10 | 8 | 7 | 3 |
| 3(D) | Zein (75%) + fenoxycarb (1%) + Soybean oil (24%) | 20 | 9 | 8 | 6 | 3 |
| 3(E) | Super Sorb (50%) + Soybean oil (50%) + PVA | 20 | 10 | 10 | 10 | 10 |
| 3(F) | Super Sorb (50%) + Soybean oil (50%) | 20 | 10 | 10 | 10 | 10 |
| 3(G) | Zein (75%) + Soybean oil (25%) + PVA | 20 | 10 | 10 | 10 | 10 |
| 3(H) | Zein (75%) + Soybean oil (25%) | 20 | 10 | 10 | 10 | 10 |
| 3(I) | Control (no formulation) | — | 10 | 10 | 10 | 10 |

[1]Test sites are in Lee County, Florida, in sandy soil with grass around mound. Mound diameters ranged from ca. 12 × 12 inches to ca. 33 × 36 inches.
[2]Powdered polymer formulations (ca. 98%) hand sprinkled around mound perimeter or directly on mound (ca. 2%) or applied in a heat-sealed 2 × 2 inch (2 mil) PVA pouch (ca. 0.75 g) adjacent to or directly on mound. Non-fenoxycarb polymer formulations considered as check/controls. Formulation bait consisted of soybean oil (Sigma Chemical Company, St. Louis, MO 63178). Rain (<1 to 6.84 inches) recorded during weeks 1, 2, 5, and 13.
[3]Test terminated at 13 weeks posttreatment at highest mortality indicated. Dead and deformed ants found in all mounds treated with fenoxycarb.

TABLE 4

Comparative efficacy of solid superabsorbent polymer-base Dursban1 ® 4E bait formulations against mixed populations of adult and nymphal stages of crickets (Gryllidae).[1]

| Test no. | Formulation ingredients per test chamber[2] (concentration) | Mean percentage reduction of crickets at indicated posttreatment time period (hrs.) | | |
|---|---|---|---|---|
| | | 6 | 20 | 27 |
| 4a | Water Lock ® A-100 (74.5%) + Dursban ® (0.25%) + peanut oil (24.25%) + potatoes (1%) | 50 | 100 | — |
| 4b | Water Lock ® A-200 (74.5%) + Dursban ® (0.25%) + peanut oil (24.25%) + potatoes (1%) | 45 | 85 | 100 |
| 4c | Water Lock ® B-204 (74.5%) + Dursban ® (0.25%) + peanut oil (24.25%) + potatoes (1%) | 40 | 95 | 100 |
| 4d | Super Sorb (74.5%) + Dursban ® (0.25%) + peanut oil (24.25%) + potatoes (1%) | 40 | 100 | — |
| 4e | Soluble starch (74.5%) + Dursban ® (0.25%) + peanut oil (24.25%) + potatoes (1%) (Check: non-superabsorbent matrix) | 35 | 100 | — |
| 4f | Water Lock ® A-100 (75%) + peanut oil (24%) + potatoes (1%) (Check/control) | 0 | 0 | 0 |
| 4g | Water Lock ® A-200 (75%) + peanut oil (24%) + potatoes (1%) (Check/control) | 0 | 5 | 5 |
| 4h | Water Lock ® B-204 (75%) + peanut oil (24%) + potatoes (1%) (Check/control) | 5 | 5 | 5 |
| 4i | Super Sorb (75%) + peanut oil (24%) + potatoes (1%) (Check/control) | 0 | 0 | 0 |
| 4j | Soluble starch (75%) + peanut oil (24%) + potatoes (1%) (Check/control) | 0 | 5 | 5 |
| 4k | Peanut oil (76%) + potatoes (24%) | 0 | 0 | 0 |

TABLE 4-continued

Comparative efficacy of solid superabsorbent polymer-base Dursban l ® 4E bait formulations against mixed populations of adult and nymphal stages of crickets (Gryllidae).[1]

| Test no. | Formulation ingredients per test chamber[2] (concentration) | Mean percentage reduction of crickets at indicated posttreatment time period (hrs.) | | |
|---|---|---|---|---|
| | | 6 | 20 | 27 |
| | (Check/control) | | | |

[1]Crickets (mixed populations of 2 species) obtained from a bait shop in Ft. Myers, Florida. Crickets ranged from ca. 18-33 mm in length.
[2]Test chambers consisted of one quart glass mason jars with screened lids. Each test chamber consisted of 10 crickets (2 replications/formulation). Total hand-mixed powdered formulation of 0.5 g applied to base perimeter of each test chamber. All formulations prepared on test day. Dursban ® 4E (Southern Mill Creek Products Company, inc., Tampa, Florida 33687) formulated at 0.00125 g per test chamber. Baits used in all formulations consisted of peanut oil (Sigma Chemical Company, St. Louis, MO 63178) and potatoes (Shur Fine ® Instant Mashed Potatoes, Shurfine - Central Corp., Northlake, IL 60164). Soluble starch (Difco Soluble Starch, "Difco Certified," Difco Laboratories, Detroit, MI) used as a non-superabsorbent matrix.

TABLE 5

Comparative efficacy of flowable superabsorbent polymer-base Dursban ® 4E bait formulations against mixed populations of adult and nymphal stages of crickets (Gryllidae).[1]

| Test No. | Formulation ingredients per test chamber[2] (concentration) | 56 Mean percentage reduction of adult and immature crickets at indicated posttreatment time period (hrs.) | |
|---|---|---|---|
| | | 6 | 20 |
| 5a | Water Lock ® A-100 (0.5%) + Dursban ® (0.25%) + peanut oil (0.5%) + potatoes (0.5%) + R.O. water (98.25%) | 85 | 100 |
| 5b | Water Lock ® A-200 (0.5%) + Dursban ® (0.25%) + peanut oil (0,5%) + potatoes (0.5%) + R.O. water (98.25%) | 80 | 100 |
| 5c | Water Lock ® B-204 (0.5%) + Dursban ® (0.25%) + peanut oil (0.5%) + potatoes (0.5%) + R.O. water (98.25%) | 65 | 100 |
| 5d | Super Sorb (0.5%) + Dursban ® (0.25%) + peanut oil (0.5%) + potatoes (0.5%) + R.O. water (98.25%) | 80 | 100 |
| 5e | Super Sorb (0.5%) + Dursban ® (0.25%) + peanut oil (0.5%) + potatoes (0.5%) + R.O. water (98.25%) | 50 | 100 |
| 5f | Aquastore ® F (0.5%) + Dursban ® (0.25%) + peanut oil (0.5%) + potatoes (0.5%) + R.O. water (98.25%) | — | 100 |
| 5g | Soluble starch (49%) + Dursban ® (0.25%) + peanut oil (0.5%) + potatoes (0.5%) + R.O. water (49.75%) (Check: non-superabsorbent matrix) | 55 | 100 |
| 5h | Water Lock ® A-100 (0.5%) + peanut oil (0.5%) + potatoes (0.5%) + R.O. water (98.5%) (Check/control) | 0 | 0 |
| 5i | Water Lock ® A-200 (0.5%) + peanut oil (0.5%) + potatoes (0.5%) + 0 R.O. water (98.5%) (Check/control) | 0 | |
| 5j | Water Lock ® B-204 (0.5%) + peanut oil (0.5%) + potatoes (0.5%) + R.O. water (98.5%) (Check/control) | 0 | 5 |
| 5k | Super Sorb (0.5%) + peanut oil (0.5%) + potatoes (0.5%) + R.O. water (98.5%) (Check/control) | 0 | 5 |
| 5l | Aquastore ® F (0.5%) + peanut oil (0.5%) + potatoes (0.5%) + R.O. water (98.5%) (Check/control) | — | 0 |
| 5m | Soluble starch (49%) + peanut oil (0.5%) + potatoes (0.5%) + R.O. water (50%) (Check/control) | 0 | 0 |

[1]Crickets (mixed populations of 2 species) obtained from a pet shop in Ft. Myers, Florida. Crickets ranged from ca. 18-33 mm in length.
[2]Test chambers consisted of one quart glass mason jars with screened lids. Each test chamber consisted of 10 crickets (2 replications/formulation). All formulations 3 days old at time of testing with the exception of 5e which was 8 days old. Total high shear formulation of 0.03 g applied to base perimeter of each test chamber. Dursban ® 4E (Southern Mill Creek Products Company, Inc., Tampa, Florida 33687) formulated at 0.000082 g per test chamber. Formulation topically applied with a pipette to a dorsal area at a central point ca. 5 mm from the front of the head capsule at a rate of ca. 0.0033 g per cricket (i.e., 0.0000082 g Dursban ® 4E per cricket). Baits used in all formulations consisted of peanut oil (Sigma Chemical Company, St. Louis, MO 63178) and potatoes (Shur Fine ® Instant Mashed Potatoes, Shurfine-Central Corp., Northlake, IL 60164). Soluble starch (Difco Soluble Starch, "Difco Certified," Difco Laboratories Detroit, MI) was used as non-superabsorbent matrix. Water used in all formulations was water purified by reverse osmosis filtration (R.O.).

TABLE 6

Comparative efficacy of solid superabsorbent polymer-base Dursban ® 4E bait formulations against larvae of the yellow mealworm *Tenebrio molitor*.[1]

| Test no. | Formulation ingredients per test chamber[2] (concentration) | Mean percentage of mealworms at indicated posttreatment time period (hrs) | |
|---|---|---|---|
| | | 7 | 23 |
| 6a | Water Lock ® A-100 (74.5%) + Dursban ® (0.25%) + peanut oil (24.25%) + potatoes (1%) | 60 | 100 |
| 6b | Water Lock ® A-200 (74.5%) + Dursban ® (0,25%) + peanut oil (24.25%) + potatoes (1%) | 85 | 100 |
| 6c | Water Lock ® B-204 (74.5%) + Dursban ® (0.025%) + peanut oil (24.25%) + potatoes (1%) | 70 | 100 |
| 6d | Super Sorb (74.5%) + Dursban ® (0.25%) + peanut oil (24.25%) + potatoes (1%) | 80 | 100 |
| 6e | Soluble starch (74.5%) + Dursban ® (0.25%) + peanut oil (24.25%) + potatoes (1%) | 60 | 100 |
| 6f | Water Lock ® A-100 (75%) + peanut oil (24%) + potatoes (1%) - (Check/control) | 0 | 5 |
| 6g | Water Lock ® A-200 (75%) + peanut oil (24%) + potatoes (1%) - (Check/control) | 0 | 0 |
| 6h | Water Lock ® B-204 (75%) + peanut oil (24%) + potatoes (1%) - (Check/control) | 0 | 5 |
| 6i | Super Sorb (75%) + peanut oil (24%) + potatoes (1%) - (Check/control) | 0 | 0 |
| 6j | Soluble starch (75%) + peanut oil (24%) + potatoes (1%) - (CHeck/control) | 0 | 5 |

TABLE 6-continued

Comparative efficacy of solid superabsorbent polymer-base Dursban ® 4E bait formulations against larvae of the yellow mealworm *Tenebrio molitor*.[1]

| Test no. | Formulation ingredients per test chamber[2] (concentration) | Mean percentage of mealworms at indicated posttreatment time period (hrs) | |
|---|---|---|---|
| | | 7 | 23 |
| 6k | Potatoes (76%) + peanut oil (24%) - (CHeck/control) | 0 | 0 |

[1]Mealworm larvae obtained from a pet shop in Ft. Myers, Florida. Mealworms ranged from ca. 19-26 mm in length.
[2]Test chambers consisted of one quart glass mason jars with screened lids. Each test chamber consisted of 10 mealworm larvae (2 applications/formulation). Total hand-mixed powdered formulation of 0.5 g applied to base perimeter of each test chamber. All formulations 1 day old at the time of testing. Dursban ® 4E (Southern Mill Creek Products Company, Inc., Tampa, FL 33678) formulated at 0.00125 g per test chamber. Baits used in all formulations consisted of peanut oil (Sigma Chemical Company, St. Louis, MO 63178) and potatoes (Shur Fine ® Instant Mashed Potatoes, Shurfine - Central Corp., Northlake, IL 60164). Soluble Starch (Difco Soluble Starch, "Difco Certified," Difco Laboratories, Detroit, MI) used as a non-superabsorbent matrix.

TABLE 7

Comparative efficacy of flowable superabsorbent polymer-base Dursban ® 4E bait formulations against larvae of the yellow mealworm *Tenebrio molitor*.[1]

| Test no. | Formulation ingredients per test chamber[2] (concentration) | Mean percentage reduction of mealworms at indicated posttreatment time period (hrs.) | |
|---|---|---|---|
| | | 7 | 23 |
| 7a | Water Lock ® A-100 (0.5%) + Dursban ® (0.25%) + peanut oil (0.5%) + potatoes (0.5%) + R.O. water (98.25%) | 70 | 100 |
| 7b | Water Lock ® A-200 (0.5%) + Dursban ® (0.25%) + peanut oil (0.5%) + potatoes (0.05%) + R.O. water (98.25%) | 95 | 100 |
| 7c | Water Lock ® B-204 (0.5%) + Dursban ® (0.25%) + peanut oil (0.5%) + potatoes (0.5%) + R.O. water (98.25%) | 100 | — |
| 7d | Super Sorb (0.5%) + Dursban ® (0.25%) + peanut oil (0.5%) + potatoes (0.5%) + R.O. water (98.25%) | 95 | 100 |
| 7e | Soluble starch (49%) + Dursban ® (0.25%) + peanut oil (0.5%) + potatoes (0.5%) + R.O. water (49.75%) | 55 | 100 |
| 7f | Water Lock ® A-100 (0.5%) + peanut oil (0.5%) + potatoes (0.5%) + R.O. water (98.5%) | 0 | 5 |
| 7g | Water Lock ® A-200 (0.5%) + peanut oil (0.5%) + potatoes (0.5%) + R.O. water (98.5%) | 0 | 0 |
| 7h | Water Lock ® B-204 (0.5%) + peanut oil (0.5%) + potatoes (0.5%) + R.O. water (98.5%) | 0 | 5 |
| 7i | Super Sorb (0.5%) + peanut oil (0.5%) + potatoes (0.5%) + R.O. water (98.5%) | 0 | 0 |
| 7j | Soluble starch (49%) + peanut oil (0.5%) + potatoes (0.5%) + R.O. water (50%) | 0 | 5 |

[1]Mealworm larvae obtained from a pet shop in Ft. Myers, FL. Mealworms ranged from ca 19-26 mm in length.
[2]Test chambers consisted of one quart glass mason jars with screened lids. Each test chamber consisted of 10 mealworm larvae (2 replications/formulation). All formulations 4 days old at the time of testing. Total high shear formulation of 0.03 g applied to base perimeter of each test chamber. Dursban ® 4E (Southern Mill Creek Products Company, Inc., Tampa, FL 336178) formulated at 0.000082 g per test chamber. Formulation topically applied with a pipette to a dorsal thoracic area at a central point ca. 5 mm from the front of the head capsule at a rate of ca. 0.0033 g per mealworm larvae (i.e., 0.0000082 g Dursban ® 4E per mealworm larvae). Baits used in all formulations consisted of peanut oil (Sigma Chemical Company, St. Louis, MO 63178) and potatoes (Shur Fine ® Instant Mashed Potatoes, Shurfine - Central Corp., Northlake, IL 60164). Soluble starch (Difco Soluble Starch, "Difco Certified," Difco Laboratories, Detroit, MI) is a non-superabsorbent matrix. Water used in all formulations was water purified by reverse osmosis filtration (R.O.).

TABLE 8

Comparative environmental persistence of technical and Arosurf ® 66-E2 - or soybean oil - formulated superabsorbent polymers exposed to natural field conditions.[1]

| Test no. | Formulation ingredient[2] (concentration) | Degradation of solid superabsorbent polymer compositions at indicated posttreatment time period (weeks)[3] based on qualitative observational scale of 0 to 10 (0 = completely decomposed or absent, 5 = 50% decomposed or absent, 10 = 100% present) | | | | | | Formulation consistency at 6 weeks posttreatment[4] |
|---|---|---|---|---|---|---|---|---|
| | | 1 | 2 | 3 | 4 | 5 | 6 | |
| 8a | Water Lock ® A-100 (50%) + Arosurf ® 66-E2 (50%) | 10 | 9 | 8 | 7 | 6 | 5 | Small hard granules |
| 8b | Super Sorb (50%) + Arosurf ® 66-E2 (50%) | 10 | 9 | 7 | 5 | 5 | 5 | Hard solidified mass |
| 8c | Aqua Keep ® J-500 (50%) + Arosurf ® 66-E2 (50%) | 10 | 10 | 9 | 9 | 9 | 9 | Unified elastomeric mass |
| 8d | Aquastore ® (80%) + Arosurf ® 66-E2 (20%) | 10 | 9 | 7 | 7 | 7 | 6 | Hard granular clumps |
| 8e | Aquastore ® F (80%) + Arosurf ® 66-E2 (20%) | 10 | 10 | 9 | 9 | 9 | 8 | Hard solidified mass |
| 8f | Aquastore ® F (80%) + Soybean oil (20%) | 10 | 9 | 7 | 5 | 4 | 3 | Hard solidified clump |
| 8g | Water Lock ® A-100 (100%) | 1 | 0[5] | — | — | — | — | — |
| 8h | Super Sorb (100%) | 0 | — | — | — | — | — | — |
| 8i | Aqua Keep ® J-500 (100%) | 1 | 0[6] | — | — | — | — | — |
| 8j | Aquastore ® (100%) | 4 | 0[7] | — | — | — | — | — |

TABLE 8-continued

Comparative environmental persistence of technical and Arosurf ® 66-E2 - or soybean oil - formulated superabsorbent polymers exposed to natural field conditions.[1]

| Test no. | Formulation ingredient[2] (concentration) | Degradation of solid superabsorbent polymer compositions at indicated posttreatment time period (weeks)[3] based on qualitative observational scale of 0 to 10 (0 = completely decomposed or absent, 5 = 50% decomposed or absent, 10 = 100% present) | | | | | | Formulation consistency at 6 weeks posttreatment[4] |
|---|---|---|---|---|---|---|---|---|
| | | 1 | 2 | 3 | 4 | 5 | 6 | |
| 8k | Aquastore ® F (100%) | 2 | 0[8] | — | — | — | — | — |

[1] All solid (powdered) formulations applied in a mound shape to a sandy soil/grassy substrate. Minimum–maximum weekly temperatures ('F.) ranged from 36–82, 44–86, 38–78, 40–84, 46–86, 6, 7, 848–82 for weeks 1–6, respectively. Rain fall (inches) of ca. <1, 1, and 0.25 was recorded in weeks, 2, 3, and 5, respectively. Climatological conditions varied from clear and sunny (high ultraviolet radiation exposure) to overcast and sunny (low ultraviolet radiation 140 exposure).
[2] All superabsorbent polymers and superabsorbent polymer-base formulations with Arosurf ® 66-E2 (2 mol ethoxylate of isostearyl alcohol; Sherex Chemical Co., Dublin, OH 43017) or soybean oil (Sigma Chemical Company, St. Louis, MO 63178) applied to natural substrate at ca. 20 g per formulation.
[3] All other comparable superabsorbent polymer-base soybean oil compositions were partially or completely removed from habitat by foraging ants prior to test termination.
[4] Some sand and other foreign particles incorporated in and/or on matricies.
[5,6,7,8] Total polymer decomposition actually occurred on day, 8, 9, 11, and 10 for test no. 7g, i, j, and k, respectively.

TABLE 9

Comparative stability of environmentally stressed solid superabsorbent-base polymer formulations of Arosurf ® 66-E2.[1]

| Test no. | Formulation ingredients[2] (concentration) | Total formulation application rate (g) | Activity or stability of 6 weeks old prestressed superabsorbent polymer-base formulations based on water surface spreading diameter (cm) of Arosurf ® 66-E2 translocated talc.[3] |
|---|---|---|---|
| 9a | Water Lock ® A-100 (50%) + Arosurf ® 66-E2 (50%) | 0.1885 | 93.98 |
| 9b | Super Sorb (50%) + Arosurf ® 66-E2 (50%) | 0.1684 | 83.36 |
| 9c | Aqua Keep ® J-500 (50%) + Arosurf ® 66-E2 (50%) | 0.1556 | 116.84 |
| 9d | Aquastore ® (80%) + Arosurf ® 66-E2 (20%) | 0.1482 | 60.96 |
| 9e | Aquastore ® F (80%) + Arosurf ® 66-E2 (20%) | 0.1417 | 73.66 |

[1] Spreading tests conducted in 100 × 50 or 50 × 50 ft. experimental ponds containing natural rain and ground water in little or no wind conditions. Arosurf ® 66-E2 used as a diluent/carrier/matrix release stabilizer and/or modifier for active agents that may be incorporated there within.
[2] Subsamples of formulations presented in Table 8 were exposed to the natural elements for ca. 6 weeks at the time of evaluation.
[3]Talc (2.45 g per test) was used as the visual indicator to determine the potential bioactive agent release activity of all test polymer-base formulations. Spreading diameter data for each formulation obtained at 2 min. posttreatment. Varying degrees of polymer swelling observed during spreading interval.

TABLE 10

Comparative subsurface translocation of superabsorbent polymer-base bait (soybean oil) formulations in mounds by workers of the imported fire ant.[1]

| Test no. (Mound ID) | Formulation ingredients[2] (concentration) | Mound diameter[3] (inches) | Presence of superabsorbent polymer-base bait formulations at indicated mound depth (inches) (+ = present, — = absent)[4] 0–2 | 2–4 | 4–6 | 6–8 | 8–10 | 10–12 |
|---|---|---|---|---|---|---|---|---|
| 10(A) | Water Lock ® A-200 (75%) + soybean oil (25%) | 8 × 7 | — | + | + | — | — | — |
| 10(B) | Water Lock ® A-200 (75%) + soybean oil (25%) | 10 × 11 | — | — | + | + | + | — |
| 11(A) | Aqua Keep ® J-500 (50%) + soybean oil (50%) | 9 × 10 | — | — | — | + | + | — |
| 11(B) | Aqua Keep ® J-500 (50%) + soybean oil (50%) | 5 × 7 | + | + | — | — | — | — |
| 12(A) | Aridall ® 1078 (75%) + soybean oil (25%) | 14 × 11 | — | + | + | + | + | — |
| 12(B) | Aridall ® 1078 (75%) + soybean oil (25%) | 12 × 12 | — | — | + | + | — | — |
| 13(A) | Super Sorb (75%) + soybean oil (25%) | 12 × 12 | + | + | — | — | — | — |
| 13(B) | Super Sorb (75%) + soybean oil (25%) | 8 × 9 | + | + | + | + | — | — |
| 14(A) | Aquastore ® (80%) + soybean oil (20%) | 10 × 12 | + | + | + | — | — | — |
| 14(B) | Aquastore ® (80%) + soybean oil (20%) | 9 × 13 | + | — | + | + | — | — |
| 15(A) | Aquastore ® F. (80%) + soybean oil (20%) | 12 × 12 | — | + | + | — | — | — |
| 15(B) | Aquastore ® F (80%) + soybean oil (20%) | 10 × 10 | — | + | + | + | — | — |

[1]Formulations scattered around sand soil/grassy perimeter of fire ant mounds.
[2]Formulation exposed to natural environment for 11 days prior to evaluations. All formulation applied at the rate of 20 g per mound. Rain (ca. 0.25 inches) recorded ca. 4 hr posttreatment. Bait used in all formulations was soybean oil (Sigma Chemical Co., St. Louis, MO 63178).
[3]Mound configuration was usually an irregularly shaped circle.
[4]Core samples exposed to water for ca. 1-3 min. Degree of swelling varied according to type of polymer and mound. Immature stages of fire ant mainly observed in region(s) of polymers.

I claim:

1. A controlled release insecticidal, pesticidal or insecticidal/pesticidal delivery composition for controlling a population of terrestrial insects or pests in a variety of natural or artificial terrestrial environments comprising: at least one superabsorbent solid organic polymer selected from the group consisting of: hydrophilic acrylamide and acrylate polymers, co-polymers and ter-polymers which absorb over 100 times their weight in water, and at lest one formulation containing an insecticidal or pesticidal agent, said polymer and agent being present in a total amount effective to control a target population of terrestrial insects and/or habitat-related/associated pests when applied to a target habitat, insect, pest, or host organism by ground and aerial application techniques; and wherein said composition is an admixture formed by mixing the superabsorbent polymer and the formulation containing an insecticidal, pesticidal, or insecticidal/pesticidal agent.

2. The controlled release insecticidal, pesticidal or insecticidal/pesticidal delivery compositions of claim 1, wherein the weight ratio of superabsorbent polymer to said formulation containing an insecticidal and/or pesticidal agent is from about 0.1:100 to about 100:0.001, the insecticidal and/or pesticidal agent being incorporated in the delivery composition for application at rates at or below those rates effective to control the target insects and/or pests that are used with the formulation containing an insecticidal agent alone.

3. The compositions of claim 1, wherein said superabsorbent polymer comprises a starch graft co-polymer or ter-polymer or a hydrophilic acrylamide, acrylic, or acrylate polymer, co-polymer or ter-polymer.

4. The composition of claim 1, wherein said superabsorbent polymer is selected from the group consisting of: an acrylamide sodium acrylate co-polymer; a hydrolyzed starch-polyacrylonitrile; 2-propenenitrile, homopolymer, hydrolyzed, sodium salt; poly (acrylamide-co-sodium acrylate); poly (2-propenamide-co-2-propenoic acid, sodium salt); starch-g-poly (acrylonitrile); starch-g-poly (acrylamide-co-sodium acrylate); a starch, acrylonitrile co-polymer; poly-2-propenoic acid, sodium salt; poly (2-propenamide-co-2-propenoic acid, sodium salt); starch-g-poly (2-propenamide-co-2-propenoic acid, potassium salt); starch-g-poly (2-propenamide-co-2-propenoic acid); starch-g-poly(2-propenamide-co-2-propenoic acid, sodium salt); starch-g-poly(2-propenamide-co-2-propenoic acid, sodium/aluminum mixed salts); starch grafted sodium polyacrylates; copolymer acrylamide acrylate; acrylic acid polymers, sodium salt; cellulosic laminates of poly-2-propenoic acid, sodium salt; crosslinked polyacrylamide copolymer; crosslinked modified polyacrylamide; crosslinked acrylics; mixtures thereof and metal salts thereof.

5. The controlled release insecticidal, pesticidal or insecticidal/pesticidal delivery composition of claim 1, wherein said composition further comprises a container for said superabsorbent solid organic polymer and said formulation containing an insecticidal agent, said container having walls made of at least one water-soluble and/or degradable material.

6. The controlled release insecticidal, pesticidal or insecticidal/pesticidal delivery composition of claim 1, further comprising: at least one compound selected from the group consisting of insecticides, larvicides, pupicides, insect growth regulators, convential toxicants, fumigants, systemics, pheromones, repellents, attractants, chemosterilants, biological control agents, microbial control agents, pathogens, parasites, miticides, acaricides, nematicides, herbicides, hormones, molluscicides, growth regulators, sterilants, avicides, rodenticides, pesticides, fungicides, bactericides, predicides, and mixture thereof.

7. The composition of claim 1, further comprising at least one adjuvant, diluent, carrier oil, surfactant, alcohol, surface-active agent, film-forming agent, baits, fertilizers, binders, deflocculating agents, oils, dispersing agents, penetrants, spreading agents, suspending agents, wetting agents, stabilizing agents, compatability agents, sticking agents, waxes, inverting oils, co-solvents, coupling agents, foams, anti-foaming agents, synthetic plastics, elastomers, synergists, natural or synthetic polymers and mixtures thereof.

8. The composition of claim 1, further comprising at least one oil, surfactant, surface-active agent or film-forming agent, wherein said agent is a vegetable-or animal-base oil or fat within which said insecticidal, or pesticidal, or insecticidal/pesticidal agent is soluble, suspendable or dispersable.

9. A controlled release insecticidal, pesticidal or insecticidal/pesticidal delivery composition for controlling a population of terrestrial insects and/or pests in a variety of natural or artificial terrestrial environments comprising: at least one superabsorbent solid organic polymer selected from the group consisting of: hydrophilic acrylamide and acrylate polymers, co-polymers and ter-polymers which absorb over 100 times their weight in water, and at least one insecticidal or pesticidal agent dissolved, suspended, or dispersed in an oil, surfactant, film-forming agent, or surface active agent and/or water, said polymer and agent being present in a total amount effective to control a target population of terrestrial insects and/or habitat-associated/related pests when applied to a target habitat, insect, pest or host, by ground or aerial application techniques; and wherein said composition is an admixture formed by mixing the superabsorbent polymer and the formulation containing an insecticidal, pesticidal or insecticidal/pesticidal agent.

10. The composition of claim 9, wherein the ratio of superabsorbent polymer to film-forming agent, surface-active agent, surfactant, or oil is from about 0.1:1 to about 100:0.01.

11. The composition of claim 9, wherein said superabsorbent polymer comprises a starch graft co-polymer or ter-polymer or a hydrophilic acrylamide, or acrylate polymer, co-polymer or ter-polymer.

12. The composition of claim 9, wherein said superabsorbent polymer is selected from the group consisting of: an acrylamide sodium acrylate co-polymer; a hydrolyzed starch-polyacrylonitile; 2-propenenitrile, homopolymer, hydrolyzed, sodium salt; poly (acrylamide-co-sodium acrylate); poly (2-propenamide-co-2-propenoic acid, sodium salt); starch-g-poly (acrylonitrile); starch-g-poly (acrylamide-co-sodium acrylate); a starch, acrylonitrile co-polymer; poly-2-propenoic acid, sodium salt; poly (2-propenamide-co-2-propenoic acid, sodium salt); starch-g-poly (2-propenamide-co-2-propenoic acid, potassium salt); starch-g-poly (2-propenamide-co-2-propenoic acid); starch-g-poly (2-propenamide-co-2-propenoic acid, sodium salt); starch-g-poly (2-propenamide-co-2-propenoic acid, sodium/aluminum mixed salts); starch grafted sodium polyacrylates; copolymer acrylamide acrylate; acrylic acid polymers, sodium salt; cellulosic laminates of poly-2-propenoic acid, sodium salt; crosslinked polyacrylamide copolymer; crosslinked modified polyacrylamide; crosslinked acrylics; mixtures thereof; and metal salts thereof.

13. The composition of claim 9, wherein said composition further comprises a container for said superabsorbent solid organic polymer and said insecticidal agent, said container having walls made of at least one water-soluble and/or degradable material.

14. The composition of claim 9, further comprising: at least one compound selected from the group consisting of insecticides, larvicides, pupicides, ovicides, insect growth regulators, convential toxicants, fumigants, systemics, pheromones, attractants, repellents, chemosterilants, biological control agents, microbial control agents, pathogens, parasites, miticides, acaricides, pesticides, nematicides, herbicides, molluscicides, growth regulators, hormones, sterilants, avicides, predicides, rodenticides, fungicides, bactericides, and mixtures thereof.

15. A method for controlling one or more population(s) of terrestrial insects and/or other habitat-associated/related pests, comprising the steps of:
preparing a controlled release insecticidal, pesticidal, or insecticidal/pesticidal delivery composition comprising at least one superabsorbent solid organic polymer selected from the group consisting of: hydrophilic acrylamide and acrylate polymers, co-polymers and ter-polymers which absorb over 100 times their weight in water, the insecticidal, pesticidal, or insecticidal/pesticidal delivery composition further comprising at least one insecticidal, pesticidal or insecticidal/pesticidal agent; said composition prepared by mixing the superabsorbent polymer and the insecticidal, pesticidal or insecticidal/pesticidal agent; and
applying said insecticidal, pesticidal, or insecticidal/pesticidal delivery composition to a target habitat, insect, and/or pest, or host, in an amount effective to control the population of terrestrial insects and/or pests in a variety of terrestrial environment areas needing insect and/or pest control treatment.

16. The method of claim 15, wherein said superabsorbent polymer is selected from the group consisting of: an acrylamide sodium acrylate co-polymer; a hydrolyzed starch-polyacrylonitrile; 2-propenenitrile, homopolymer hydrolyzed, sodium salt; poly (acrylamide-co-sodium acrylate); poly (2-propenamide-co-2-propenoic acid, sodium slat); starch-g-poly (acrylonitrile); starch-g-poly (acrylamide-co-sodium acrylate); a starch, acrylonitrile co-polymer, poly-2-propenoic acid, sodium salt; poly (2-propenamide-co-2-propenoic acid, sodium salt; starch-g-poly (2-propenamide-co-2-propenoic acid potassium salt); starch-g-poly (2-propenamide-co-2-propenoic acid); starch-g-poly (2-propenamide-co-2-propenoic acid, sodium salt); starch-g-poly (2-propenamide-co-2-propenoic acid, sodium/aluminum mixed salts); starch grafted sodium polyacrylates; copolymer acrylamide acrylate; acrylic acid polymers, sodium salt; cellulosic laminates of poly-2-propenoic acid, sodium salt; crosslinked polyacrylamide copolymer; crosslinked modified polyacrylamide; crosslinked acrylics; mixtures thereof; and metal salts thereof.

17. The method of claim 15, wherein said insecticidal or pesticidal composition comprises at least one film-forming agent, surface-active agent, surfactant, or oil.

18. The method of claim 15, wherein said delivery composition further comprises: at least one compound selected from the group consisting of insecticides, larvicides, pupicides, ovicides, insect growth regulators, conventional toxicants, fumigants, systemics, pheromones, attractants, repellents, chemosterilants, biological control agents, microbial control agents, pathogens, parasites, miticides, acaricides, pesticides, nematicides, herbicides, molluscicides, growth regulators, hormones, sterilants, avicide, predicides, rodenticides, fungicides, bactericides, and mixture thereof.

19. The method of claim 18, further comprising, prior to applying said composition to said terrestrial environment area, agglomerating said solid superabsorbent polymer and said insecticidal and/or pesticidal agent to produce granules, pellets, briquets, extrusions, or other various shaped solid insecticidal, pesticidal or insecticidal/pesticidal controlled release delivery compositions.

20. The method of claim 18 wherein the composition further comprises an additive bait material.

21. The method of claim 20, wherein the composition includes a hydrophobic oil, surfactant, surface-active agent, or film-forming agent, to control the insecticide, pesticide, or insecticide/pesticide release rate.

22. The method of claim 20 wherein said composition is applied as a particulate or agglomerate for the control of foraging insects.

23. The method of claim 22 wherein said composition is applied for the control of ants.

24. The method of claim 22 wherein said composition is applied for the control of red or black imported fire ants.

25. A method for controlling one or more population(s) of terrestrial insects and/or other habitat-related/associated pests, comprising:
preparing a superabsorbent polymer composition comprising at least one superabsorbent solid organic polymer selected from the group consisting of: hydrophilic acrylamide and acrylate polymers, co-polymers and ter-polymers which absorb over 100 times their weight in water, and,
applying said superabsorbent polymer composition to an active pest or insect breeding medium or environment in an amount effective to control adult pests or the emergence of adult insects and prevent the breeding of immature stages of such insects or pests.

26. The composition of claim 13 wherein said walls of said container are made of a material selected from at least one of the group consisting of polyvinyl alcohol, polyethylene oxide and hydroxypropyl methyl cellulose.

27. The controlled release composition of claim 1 wherein said composition further contains water at a polymer to water ratio of about 0.0001:100 to 1:1.

* * * * *

UNITED STATES PATENT AND TRADEMARK OFFICE
CERTIFICATE OF CORRECTION

PATENT NO. : 4,983,390                                   Page 1 of 9

DATED      : January 8, 1991

INVENTOR(S) : Richard Levy

It is certified that error appears in the above-identified patent and that said Letters Patent is hereby corrected as shown below:

On the title page: Item [54]:

The first word in the title should read --Terrestrial--. and In Column 1 line 1 the first worrd in the title should read --Terrestrial--.
In Other Publications: Page 2, Column 1, line 10, change "Bureaue" to
--Bureau--.
    line 22, change "E'" to --E"--.
    line 25, change "of" to --for--.
    line 26, before "Haas" insert --and--.
    lines 27 and 28, change "Sorb" to --Sorb™-- each occurrence.
    line 48, delete "f" and insert --™--.

Other Publications: Page 2, Column 2, line 21, change "Aquastore" to --"Aquastore--.
    line 22, change "Aid" to --Aid"-- and change "Aquastore" to "Aquastore--.
    line 23, after "." (a period) insert --"--.
    line 52, change "UPTAKE" to --Uptake--.
    line 53, change "lemna Minor" to --Lemna minor--.

Other Publications: Page 3, Column 1, lines 45 and 46, change "Var. Israe-lensis" to --var. israelensis--.
    line 50, change "Var. Israelensis" to --var. israelensis--.
    Column 2, line 6, after "as" insert --a--.
    lines 21 and 22, change "P, Edisol-m, Em-1100, QSA 2000 and Mono" to --P," "Edisol-m," "EM-1100," "QSA 2000" and "Mono--.
    line 23, change "Diet" to --Diets--.
    line 34, change "Sorb" to --Sorb™--;
    line 35, change "Sorb" to --Sorb™--;
    line 36, change "Lock" to --Lock®--
    line 38, change "502S" to --502s--.
    line 53, change "Whitemore" to --Whitmore--.

UNITED STATES PATENT AND TRADEMARK OFFICE
CERTIFICATE OF CORRECTION

PATENT NO. : 4,983,390                                     Page 2 of 9

DATED : January 8, 1991

INVENTOR(S) : Richard Levy

It is certified that error appears in the above-identified patent and that said Letters Patent is hereby corrected as shown below:

Other Publications: Page 3, Column 2, line 61, change "85," to —85.
Page 4, Column 1, line 6, change "Technology" to —Technical—.
line 8, change "taeniarhynchus" to —taeniorhynchus—
line 25, change "Var. Israelensis" to —Var. israelensis—. and delete "the".
line 41, change "Culex and Psorophora" to —Culex and Psorophora—.
Page 4, Column 2, line 17, change "Aro-surf" to —Arosurf—.
line 30, change "Release" to —release—.

Column 2, line 34, after "herbicide" insert —,—.
line 35, delete —,—.
line 41, change "al" to —al.,—.
Column 4, line 62, after "zation" insert —,—.
Column 6, line 48, change ",," to —,—.
Column 10, line 14, change "are" to —is—.
Column 11, line 19, delete "," (comma).
Column 12, lines 9 and 10, change "Sorb" to —Sorb™—
line 16, change "poly (2" to —poly (2—.
line 19, change "poly (2" to —poly (2—.
line 20, after "acid," insert —sodium salt), (Water Lock® Superabsorbent Polymer A-200)—.
line 21, change "poly (2" to —poly (2—.
line 22, change "salt" to —salts—.
line 23, delete "Sodium" and after "A-222)" insert —;—

UNITED STATES PATENT AND TRADEMARK OFFICE
CERTIFICATE OF CORRECTION

PATENT NO. : 4,983,390

DATED : January 8, 1991

INVENTOR(S) : Richard Levy

It is certified that error appears in the above-identified patent and that said Letters Patent is hereby corrected as shown below:

Column 12, lines 24 and 25, delete in their entirety;

line 26, change "poly　(2" to --poly (2--;

line 36, align margin;

line 38, insert --(-- at beginning of line;

line 39, change "5025" to --502s--;

line 42, change "cross-linked" to --crosslinked--;

line 47, change "cross-linked" to --crosslinked--;

line 49 after "nontoxic" insert --,-- (comma); and line 65, change "1986-86" to --1985-86--.

UNITED STATES PATENT AND TRADEMARK OFFICE
CERTIFICATE OF CORRECTION

PATENT NO. : 4,983,390
DATED : January 8, 1991
INVENTOR(S) : Richard Levy

It is certified that error appears in the above-identified patent and that said Letters Patent is hereby corrected as shown below:

Column 14, line 15, change "Pathoo" to --Pathog--; and line 41, change "Aridal" to --Aridall--.

Column 15, line 54, change "PH" to --pH--.

Column 17, line 3, change "PH" to --pH--;

line 34, change "PH" to --pH--; and line 43, at end of line, insert --.-- (period).

Column 18, line 13, change "a" to --or--; and line 49, change "granula" to --granular--.

Column 19, line 17, change "qermanica" to --germanica--; and

UNITED STATES PATENT AND TRADEMARK OFFICE
CERTIFICATE OF CORRECTION

PATENT NO. : 4,983,390

DATED : January 8, 1991

INVENTOR(S) : Richard Levy

It is certified that error appears in the above-identified patent and that said Letters Patent is hereby corrected as shown below:

line 50, change "Aquastor" to --Aquastore--.

Column 20, line 62, change "or" to --of--.

Column 22, line 57, change "E2--or" to --E2-or-- and "oil--formulated" to --oil-formulated--.

Table 1, Column 23, line 32, change "0.05%" to --0.5%--.

Table 2, Column 26, line 9, align 10 under 8 and 9.

Table 4, Column 26, line 1, delete "1" and correct spacing to read --Dursban®4E--; and line 4, change "hrs." to --hrs--.

Column 28, line 1, delete "1" and correct spacing to read --Dursban®4E--; and line 4, change "hrs." to --hrs--.

UNITED STATES PATENT AND TRADEMARK OFFICE
CERTIFICATE OF CORRECTION

PATENT NO. : 4,983,390
DATED : January 8, 1991
INVENTOR(S) : Richard Levy

It is certified that error appears in the above-identified patent and that said Letters Patent is hereby corrected as shown below:

Table 5, Column 28, line 3, delete "56";

line 6, change "hrs." to --hrs--;

line 10, change "0,5%" to --0.5%--; and line 24, insert tab between "+" and "0"

to correct alignment problem.

Table 6, Column 28, line 3, before "of" insert --reduction--;

line 10, change "0.025%" to --0.25%--;

and line 17, change "CHeck" to --Check--.

Column 30, line 3, before "of" insert --reduction--;

and line 8, change "CHeck" to --Check--.

Table 7, Column 30, line 6, change "hrs." to --hrs--;

line 10, change "0.05%" to --0.5%;

line 16, insert tab between "+" and "55"

to correct alignment problem;

line 23, change "ca" to --ca.--; and

UNITED STATES PATENT AND TRADEMARK OFFICE
CERTIFICATE OF CORRECTION

PATENT NO. : 4,983,390
DATED : January 8, 1991
INVENTOR(S) : Richard Levy

It is certified that error appears in the above-identified patent and that said Letters Patent is hereby corrected as shown below:

line 26, change "336178" to --33687--.

Table 8, Column 31, line 13, change "6, 7, 848" to --48--.

Column 32, line 12, change "°F." to --°F--; and line 14, delete "140".

Table 9, Column 32, line 4, change "weeks" to --week--.

Claim 1, Column 32, line 63, change "lest" to --least--.

Claim 3, Column 33, line 17, delete "or" (second occurrence).

Claim 4, Column 33, line 29, change "poly (2" to --poly (2--.

Claim 6, Column 33, line 51, before "insect" insert --ovicides--.

Claim 7, Column 33, lines 61-67, change all words in the plural form to the singular form;

line 68, change "mers" to --mer,--.

UNITED STATES PATENT AND TRADEMARK OFFICE
CERTIFICATE OF CORRECTION

PATENT NO. : 4,983,390
DATED : January 8, 1991
INVENTOR(S) : Richard Levy

It is certified that error appears in the above-identified patent and that said Letters Patent is hereby corrected as shown below:

Claim 9, Column 34, line 17, change "surface active" to --surface-active--.

Claim 11, Column 34, line 33, delete "or" (second occurrence) and insert --acrylic,--.

Claim 12, Column 34, line 45, change "poly (2" to --poly (2--.

Claim 16, Column 35, line 32, change "slat" to --salt--;

line 34, change "," (comma) to --;-- (semi-colon); and line 36, after "acid" insert --,--.

Claim 18, Column 36, line 6, change "avicide" to --avicides--.

UNITED STATES PATENT AND TRADEMARK OFFICE
CERTIFICATE OF CORRECTION

PATENT NO. : 4,983,390

DATED : January 8, 1991

INVENTOR(S) : Richard Levy

It is certified that error appears in the above-identified patent and that said Letters Patent is hereby corrected as shown below:

Column 36, line 7, change "mixture" to --mixtures--.

Signed and Sealed this

Twenty-first Day of September, 1993

Attest:

BRUCE LEHMAN

*Attesting Officer*       *Commissioner of Patents and Trademarks*